United States Patent
Russell

(10) Patent No.: US 9,993,276 B2
(45) Date of Patent: Jun. 12, 2018

(54) BONE SCREWS AND METHODS OF USE THEREOF

(71) Applicant: InnoVision, Inc., Memphis, TN (US)

(72) Inventor: Thomas A. Russell, Memphis, TN (US)

(73) Assignee: Innovision, Inc., Memphis, TN (US)

( * ) Notice: Subject to any disclaimer, the term of this patent is extended or adjusted under 35 U.S.C. 154(b) by 652 days.

(21) Appl. No.: 14/398,172

(22) PCT Filed: Mar. 5, 2014

(86) PCT No.: PCT/US2014/020678
§ 371 (c)(1),
(2) Date: Oct. 31, 2014

(87) PCT Pub. No.: WO2014/149746
PCT Pub. Date: Sep. 25, 2014

(65) Prior Publication Data
US 2015/0272646 A1  Oct. 1, 2015

Related U.S. Application Data

(60) Provisional application No. 61/801,804, filed on Mar. 15, 2013.

(51) Int. Cl.
*A61B 17/86* (2006.01)
*A61B 17/88* (2006.01)
(Continued)

(52) U.S. Cl.
CPC ...... *A61B 17/8811* (2013.01); *A61B 17/7098* (2013.01); *A61B 17/863* (2013.01);
(Continued)

(58) Field of Classification Search
CPC ..... A61B 17/86; A61B 17/863; A61B 17/864; F16B 25/0078
(Continued)

(56) References Cited

U.S. PATENT DOCUMENTS

| 2,414,882 A | 1/1947 | Longfellow |
| 2,570,465 A | 10/1951 | Lundholm |

(Continued)

FOREIGN PATENT DOCUMENTS

| CA | 1227902 A | 10/1987 |
| CA | 2076501 C | 6/1996 |

(Continued)

OTHER PUBLICATIONS

"European Application Serial No. 14767460.0, Extended European Search Report dated Jan. 13, 2017", 9 pgs.
(Continued)

*Primary Examiner* — Nicholas Woodall
(74) *Attorney, Agent, or Firm* — Schwegman Lundberg & Woessner, P.A.

(57) ABSTRACT

The invention features improved bone screws, a delivery manifold for delivering a flowable medium to a bone screw, and washers for use with the bone screw to provide compressive fixation. The invention also features methods of treatment using the bone screws, washers, and/or delivery manifold, and kits that include the same.

16 Claims, 20 Drawing Sheets

(51) Int. Cl.
    *A61B 17/70*           (2006.01)
    *F16B 25/00*           (2006.01)

(52) U.S. Cl.
    CPC ........ *A61B 17/864* (2013.01); *A61B 17/8695* (2013.01); *A61B 17/8841* (2013.01); *F16B 25/0078* (2013.01)

(58) Field of Classification Search
    USPC ...................................................... 411/421
    See application file for complete search history.

(56) References Cited

U.S. PATENT DOCUMENTS

| | | | |
|---|---|---|---|
| 3,554,193 A | 1/1971 | Konstantinou et al. | |
| 4,479,271 A | 10/1984 | Bolesky et al. | |
| 4,494,535 A | 1/1985 | Haig | |
| 4,640,271 A | 2/1987 | Lower | |
| 4,653,489 A | 3/1987 | Tronzo | |
| 4,756,307 A | 7/1988 | Crowninshield | |
| 4,781,181 A | 11/1988 | Tanguy | |
| 4,860,513 A | 8/1989 | Whitman | |
| 4,950,270 A | 8/1990 | Bowman et al. | |
| RE33,348 E | 9/1990 | Lower | |
| 5,019,079 A | 5/1991 | Ross | |
| 5,047,030 A | 9/1991 | Draenert | |
| 5,122,141 A | 6/1992 | Simpson et al. | |
| 5,129,901 A | 7/1992 | Decoste | |
| 5,143,498 A | 9/1992 | Whitman | |
| 5,147,406 A | 9/1992 | Houston et al. | |
| 5,152,792 A | 10/1992 | Watkins et al. | |
| 5,156,606 A | 10/1992 | Chin | |
| 5,167,664 A | 12/1992 | Hodorek | |
| 5,169,400 A | 12/1992 | Muhling et al. | |
| 5,180,382 A | 1/1993 | Frigg et al. | |
| 5,190,551 A | 3/1993 | Chin et al. | |
| 5,192,282 A | 3/1993 | Draenert | |
| 5,209,805 A | 5/1993 | Spraggins | |
| 5,214,987 A | 6/1993 | Fenton, Sr. | |
| 5,222,957 A | 6/1993 | McColl et al. | |
| 5,222,958 A | 6/1993 | Chin | |
| 5,249,899 A | 10/1993 | Wilson | |
| 5,324,292 A | 6/1994 | Meyers | |
| 5,334,204 A | 8/1994 | Clewett et al. | |
| 5,338,197 A | 8/1994 | Kwan | |
| 5,344,654 A | 9/1994 | Rueger et al. | |
| 5,354,557 A | 10/1994 | Oppermann et al. | |
| 5,383,878 A | 1/1995 | Roger et al. | |
| 5,391,181 A | 2/1995 | Johnson et al. | |
| 5,484,440 A | 1/1996 | Allard | |
| 5,484,445 A | 1/1996 | Knuth | |
| 5,489,143 A | 2/1996 | Adachi et al. | |
| 5,496,319 A | 3/1996 | Allard et al. | |
| 5,534,027 A | 7/1996 | Hodorek | |
| 5,534,032 A | 7/1996 | Hodorek | |
| 5,536,127 A | 7/1996 | Pennig | |
| 5,573,548 A | 11/1996 | Nazre et al. | |
| 5,601,559 A | 2/1997 | Melker et al. | |
| 5,649,931 A | 7/1997 | Bryant et al. | |
| 5,658,285 A | 8/1997 | Marnay et al. | |
| 5,725,581 A * | 3/1998 | Brangnemark | A61B 17/8625 411/386 |
| 5,743,912 A | 4/1998 | Lahille et al. | |
| 5,783,217 A | 7/1998 | Lee et al. | |
| 5,788,702 A | 8/1998 | Draenert | |
| 5,854,207 A | 12/1998 | Lee et al. | |
| 5,938,664 A | 8/1999 | Winquist et al. | |
| 6,016,727 A | 1/2000 | Morgan | |
| 6,027,742 A | 2/2000 | Lee et al. | |
| 6,036,491 A | 3/2000 | Hansson | |
| 6,048,343 A | 4/2000 | Mathis et al. | |
| 6,066,142 A | 5/2000 | Serbousek et al. | |
| 6,210,376 B1 | 4/2001 | Grayson | |
| 6,214,012 B1 * | 4/2001 | Karpman | A61B 17/864 606/246 |
| 6,214,368 B1 | 4/2001 | Lee et al. | |
| 6,287,341 B1 | 9/2001 | Lee et al. | |
| 6,319,270 B1 | 11/2001 | Grafton et al. | |
| 6,331,312 B1 | 12/2001 | Lee et al. | |
| 6,436,100 B1 | 8/2002 | Berger | |
| 6,440,136 B1 | 8/2002 | Gambale et al. | |
| 6,541,037 B1 | 4/2003 | Lee et al. | |
| 6,565,572 B2 | 5/2003 | Chappius | |
| 6,604,945 B1 | 8/2003 | Jones | |
| 6,610,079 B1 | 8/2003 | Li et al. | |
| 6,635,059 B2 | 10/2003 | Randall et al. | |
| 6,682,531 B2 | 1/2004 | Winquist et al. | |
| 6,755,835 B2 | 6/2004 | Schultheiss et al. | |
| 6,863,671 B1 | 3/2005 | Strobel et al. | |
| 6,869,283 B2 | 3/2005 | Sussman | |
| 6,875,218 B2 | 4/2005 | Dye et al. | |
| 6,875,237 B2 | 4/2005 | Dye | |
| 6,890,335 B2 | 5/2005 | Grabowski et al. | |
| 6,893,447 B2 | 5/2005 | Dominguez et al. | |
| 6,918,912 B2 | 7/2005 | Seemann | |
| 6,953,594 B2 | 10/2005 | Lee et al. | |
| 6,962,593 B2 | 11/2005 | Sanford et al. | |
| 6,972,130 B1 | 12/2005 | Lee et al. | |
| 6,989,014 B2 | 1/2006 | Justin et al. | |
| 7,011,664 B2 | 3/2006 | Haney et al. | |
| 7,037,309 B2 | 5/2006 | Weil et al. | |
| 7,150,879 B1 | 12/2006 | Lee et al. | |
| 7,198,627 B2 | 4/2007 | Bagga et al. | |
| 7,258,692 B2 | 8/2007 | Thelen et al. | |
| 7,261,716 B2 | 8/2007 | Strobel et al. | |
| 7,300,439 B2 | 11/2007 | May | |
| 7,306,605 B2 | 12/2007 | Ross | |
| 7,316,687 B2 | 1/2008 | Aikins et al. | |
| 7,318,841 B2 | 1/2008 | Tofighi et al. | |
| 7,328,131 B2 | 2/2008 | Donofrio et al. | |
| 7,335,201 B2 | 2/2008 | Doubler et al. | |
| 7,338,493 B1 | 3/2008 | Vandewalle | |
| 7,354,442 B2 | 4/2008 | Sasso et al. | |
| 7,488,320 B2 | 2/2009 | Middleton | |
| 7,517,539 B1 | 4/2009 | Lee et al. | |
| 7,520,880 B2 | 4/2009 | Claypool et al. | |
| 7,608,097 B2 | 10/2009 | Kyle | |
| 7,637,929 B2 | 12/2009 | Auth | |
| 7,717,947 B1 * | 5/2010 | Wilberg | A61B 17/7098 606/304 |
| 7,727,236 B2 | 6/2010 | Choe et al. | |
| 7,731,738 B2 | 6/2010 | Jackson et al. | |
| 7,892,265 B2 | 2/2011 | Perez-Cruet et al. | |
| 7,951,179 B2 | 5/2011 | Matityahu | |
| 8,231,632 B1 * | 7/2012 | Jordan | A61B 17/8816 606/304 |
| 8,574,273 B2 | 11/2013 | Russell et al. | |
| 2001/0021852 A1 | 9/2001 | Chappius | |
| 2003/0045881 A1 | 3/2003 | Barouk et al. | |
| 2004/0225292 A1 | 11/2004 | Sasso et al. | |
| 2005/0015061 A1 | 1/2005 | Sweeney | |
| 2005/0021084 A1 | 1/2005 | Lu et al. | |
| 2005/0027301 A1 | 2/2005 | Stihl | |
| 2005/0107800 A1 | 5/2005 | Frankel et al. | |
| 2006/0098851 A1 | 5/2006 | Shoham et al. | |
| 2006/0247642 A1 | 11/2006 | Stone et al. | |
| 2010/0004656 A1 | 1/2010 | Dos Jr. | |
| 2011/0060373 A1 | 3/2011 | Russell et al. | |
| 2011/0125265 A1 * | 5/2011 | Bagga | A61B 17/68 623/16.11 |
| 2012/0053639 A1 | 3/2012 | Grant | |
| 2012/0197311 A1 | 8/2012 | Kirschman | |
| 2012/0209334 A1 | 8/2012 | Lewis et al. | |
| 2013/0144344 A1 * | 6/2013 | Giancola | A61B 17/7098 606/304 |
| 2014/0031791 A1 | 1/2014 | Russell et al. | |
| 2015/0127056 A1 * | 5/2015 | Roybal | A61B 17/8888 606/279 |

FOREIGN PATENT DOCUMENTS

| | | |
|---|---|---|
| CA | 2057957 C | 10/1998 |
| CA | 2289152 A1 | 5/2000 |
| CA | 2413325 A1 | 1/2002 |

(56) References Cited

FOREIGN PATENT DOCUMENTS

| | | |
|---|---|---|
| CA | 2417662 A1 | 2/2002 |
| CA | 2062012 C | 4/2003 |
| CA | 2524797 A1 | 11/2004 |
| CA | 2109850 C | 1/2005 |
| CA | 2626145 A1 | 5/2007 |
| CA | 2243086 C | 6/2007 |
| CA | 2405230 C | 11/2007 |
| CA | 2390912 C | 1/2008 |
| CA | 2467262 C | 7/2008 |
| CA | 2394072 C | 8/2008 |
| CA | 2405782 C | 8/2008 |
| CA | 2449354 C | 5/2009 |
| CA | 2407108 C | 1/2010 |
| CA | 2405127 C | 2/2010 |
| CA | 2736891 A1 | 3/2010 |
| CA | 2742077 A1 | 5/2010 |
| CA | 2744392 A1 | 6/2010 |
| CA | 2506653 C | 4/2011 |
| DE | 2818254 A1 | 10/1979 |
| DE | 3434807 A1 | 12/1985 |
| DE | 19540180 A1 | 5/1996 |
| DE | 19949285 A1 | 5/2001 |
| EP | 0172130 A2 | 2/1986 |
| EP | 0451932 A1 | 10/1991 |
| FR | 2744010 A1 | 8/1997 |
| JP | H7-51292 A | 2/1995 |
| JP | H7-222752 A | 8/1995 |
| JP | 10211213 A | 8/1998 |
| JP | 2003159258 A | 6/2003 |
| WO | WO-88/06023 A1 | 8/1988 |
| WO | WO-89/09030 A1 | 10/1989 |
| WO | WO-01/17447 A1 | 3/2001 |
| WO | WO-01/26568 A1 | 4/2001 |
| WO | WO-2014149746 A1 | 9/2014 |

OTHER PUBLICATIONS

"European Application Serial No. 14767460.0, Partial European Search Report dated Oct. 7, 2016", 7 pgs.
"European Application Serial No. 14767460.0, Response filed Apr. 20, 2016 to Communication pursuant to Rules 161 (2) and 162 EPC dated Oct. 22, 2015", 18 pgs.
International Search Report and Written Opinion for International Patent Application No. PCT/US2014/020678, dated Jun. 23, 2014 (13 pages).
Chappuis et al., "Fixation strength studies with fenestrated cemented pedicle screws in human cadaver," Poster Exhibit, Sixteenth Annual Meeting North American Spine Society, Seattle, WA, Oct. 2001, (4 pages).
Tsuchiya et al., "Cannulation of simple bone cysts," J Bone Joint Surg Br. 84(2):245-8 (2002).
Innovision, Inc. 510 (k) Summary, dated Jul. 28, 2011 (5 pages).
Office Action and Machine English Translation (Google translate) for German Patent Application No. 102011112890.9, dated May 8, 2015 (14 pages).
Examination Report for Australian Patent Application No. 2011218783, dated Dec. 8, 2014 (3 pages).
Examination Report for Australian Patent Application No. 2011218783, dated Oct. 25, 2013 (4 pages).
EPO Communication pursuant to Rules 161(2) and 162 EPC for European Application No. 14767460.0, dated Oct. 22, 2015 (2 pages).
International Preliminary Report on Patentability and Written Opinion for International Application No. PCT/US2014/020678, dated Sep. 15, 2015 (8 pages).
International Search Report and Written Opinion for International Appleiation No. PCT/US14/55497, dated Jan. 2, 2015 (15 pages).
"European Application Serial No. 14767460.0, Response filed Jul. 27, 2017 to Extended European Search Report dated Jan. 13, 2017", 19 pgs.
Dickman, CA, et al., "Cannulated Screws for Odontoid Screw Fixation and Atlantoaxial Transarticular Screw Fixation. Technical Note.", J. Neurosurg. 83(6),1095-100, Abstract Only, (Dec. 1995), 1 pg.
Trumble, et al., "Displaced Scaphoid Fractures Treated With Open Reduction and Internal Fixation With a Cannulated Screw", The Journal of Bone and Joint Surgery; vol. 82-A, No. 5, (May 2000), 633-641.
"Australian Application Serial No. 2014237911, First Examination Report dated Dec. 8, 2017", 3 pgs.
"Australian Application Serial No. 2014237911, Response filed Jan. 10, 2018 to First Examination Report dated Dec. 8, 2017", 23 pgs.
"Japanese Application Serial No. 2016-500655, Office Action dated Oct. 31, 2017", w/ partial English Translation, 9 pgs.

* cited by examiner

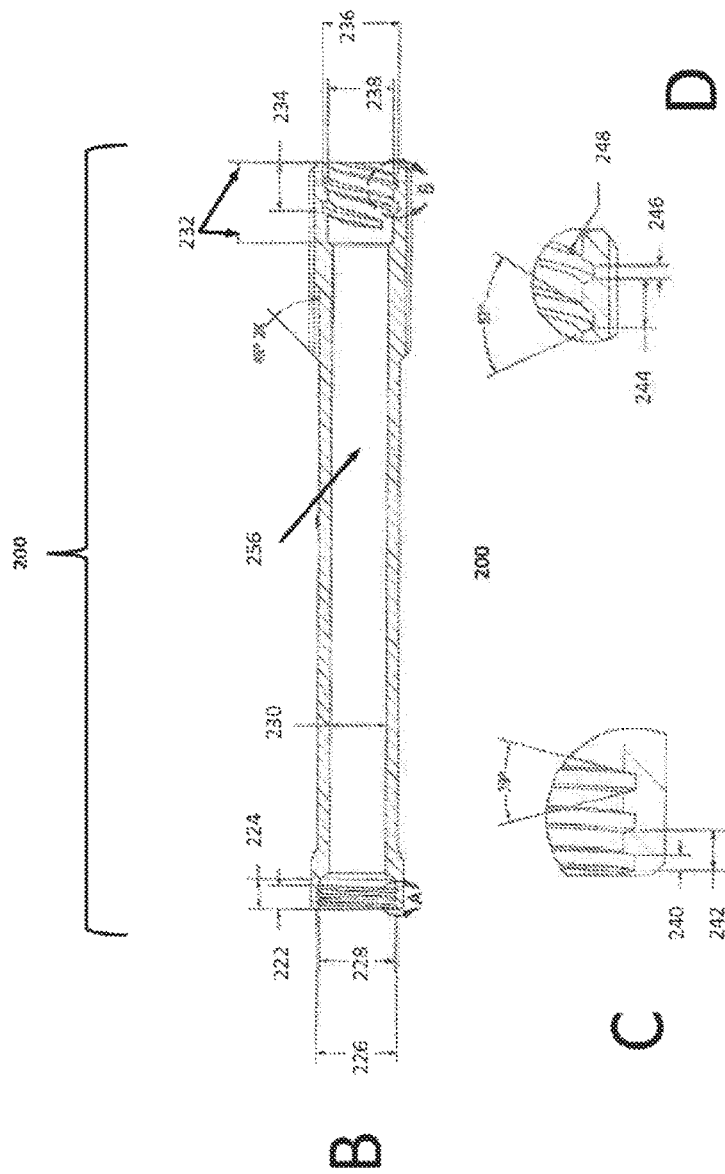

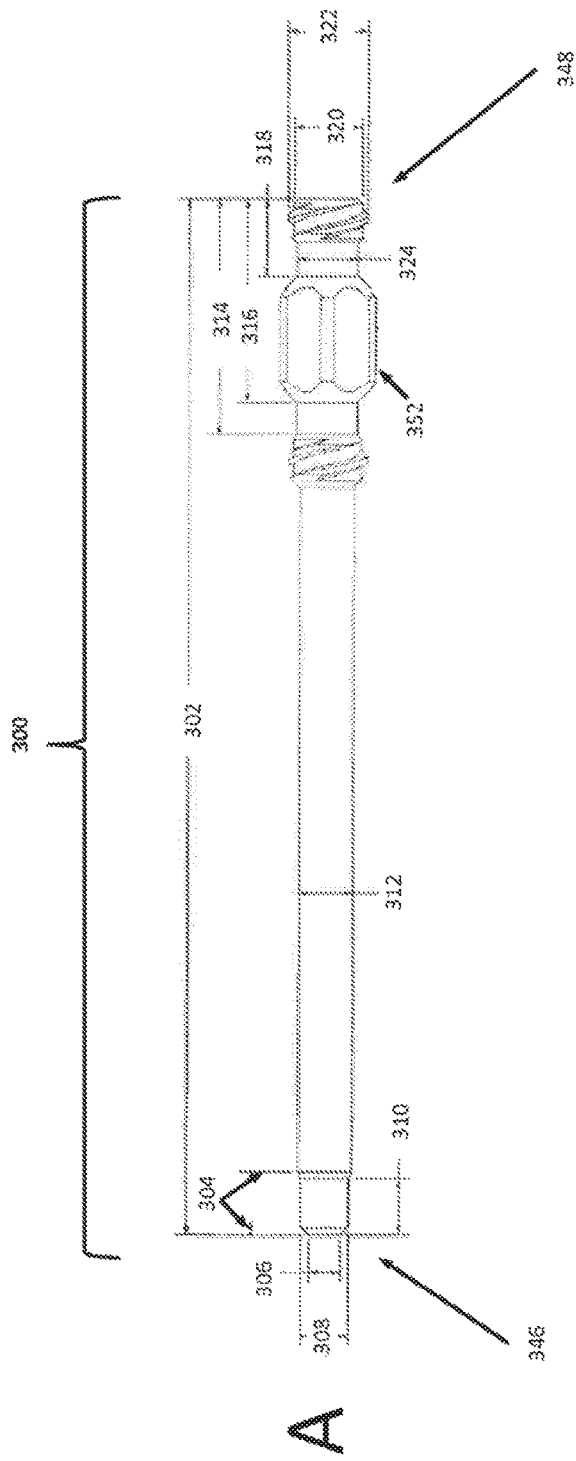

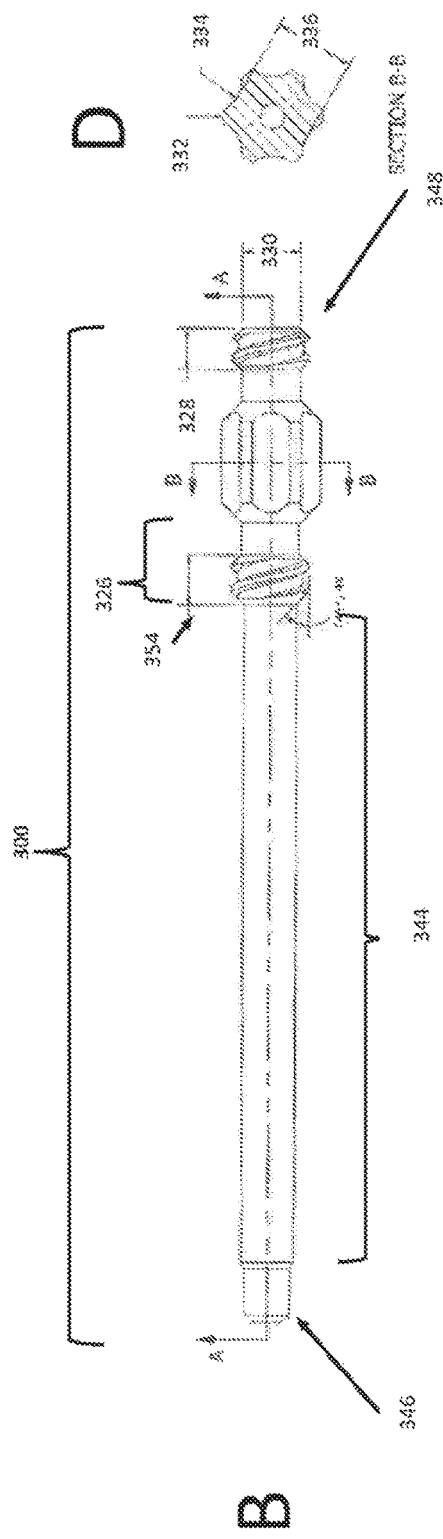
Fig. 7 (Con't)

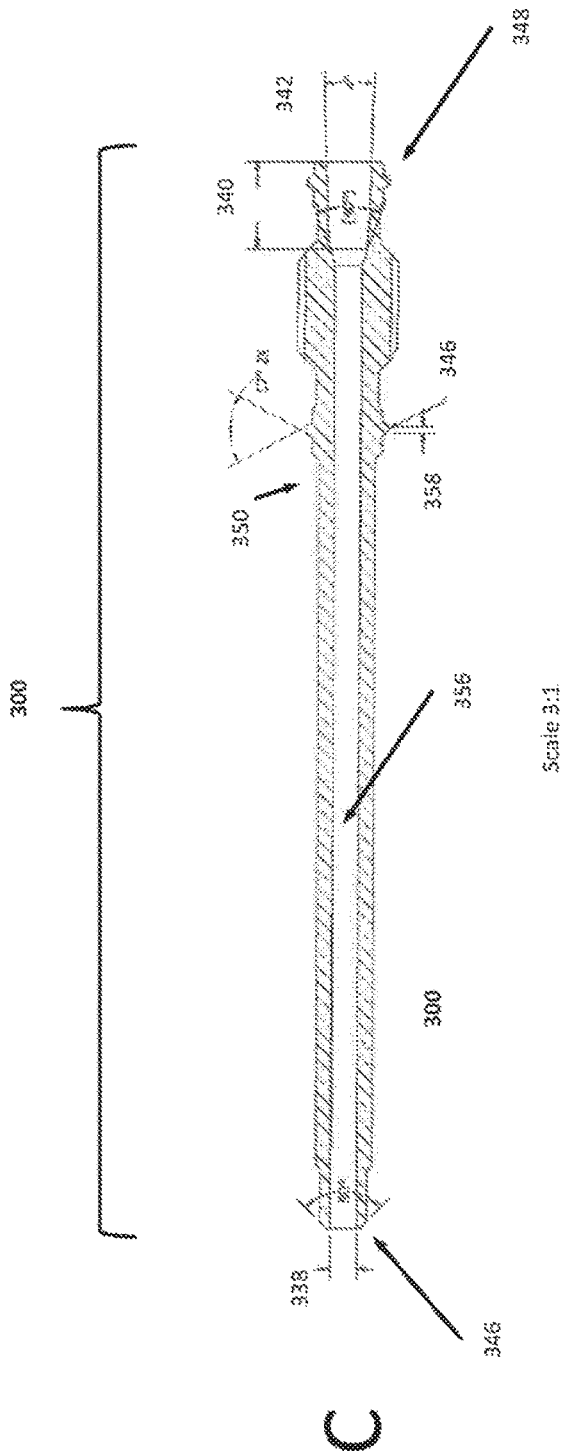

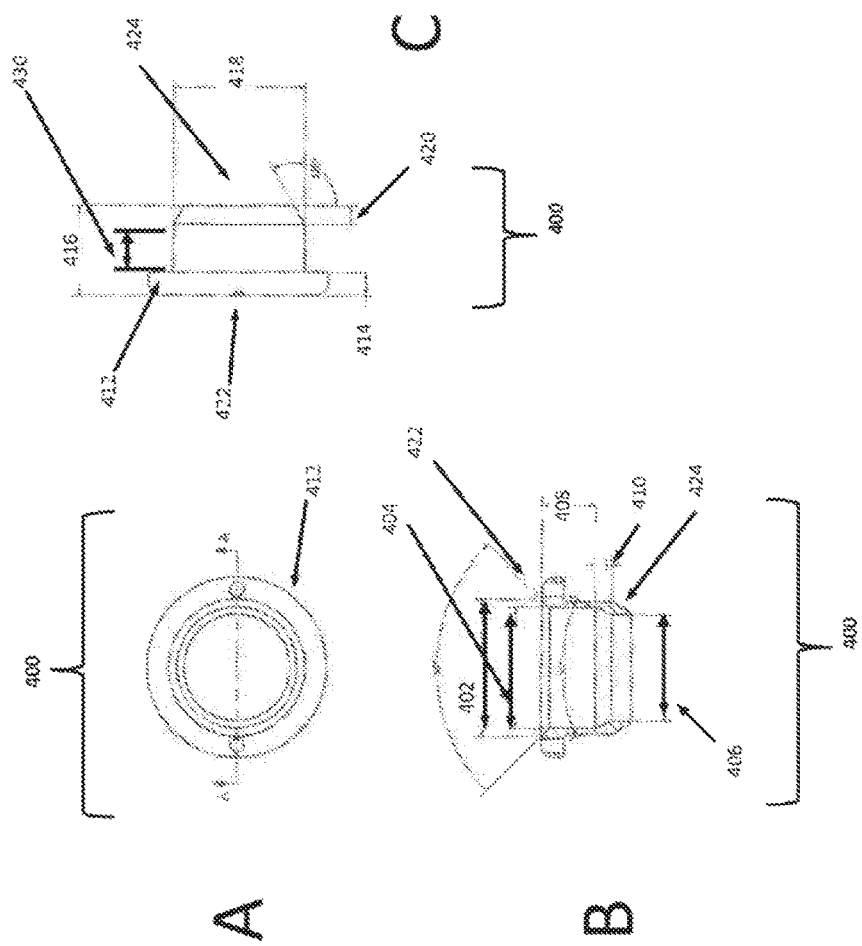

BONE SCREWS AND METHODS OF USE THEREOF

FIELD OF THE INVENTION

The invention relates to devices, in particular, bone screws, washers and bone screw manifolds and methods of use thereof for the treatment of bone defects.

BACKGROUND OF THE INVENTION

Fixation tools and devices, which are available in a wide variety of different shapes and sizes, have long been used in the repair of bone defects, such as bone fractures. A physician typically sets the bone to be repaired in the proper position and then uses the fixation tools and devices to secure the bone in that position during the healing process.

A fixation device, such as a bone plate or rod, can be secured to the bone by a fixation tool, such as a bone screw. Alternatively, a bone screw can be used by itself to repair a bone defect. One drawback associated with prior art bone screws is the potential for the bone screw to back out after implantation. To inhibit back out, bone screws have been modified with various thread designs and locking features, with some success.

When installing a bone anchor or screw, a surgeon will typically tap a hole, remove the tap and then install the screw into the hole while maintaining the alignment of the bone with another bone or prosthesis. The bone screw can be secured in the bony bed by filling the hole before installation of the screw with a bone cement, such as polymethylmethacrylate or other fillable and flowable materials.

The use of a solid screw with a bone cement or other fillable material may increase the initial stiffness and strength of the repair, but may not significantly decrease loosening of the screw at the repair site. The substitution of solid screws with cannulated screws that can extrude a bone cement or other fillable material may improve the strength of the repair while at the same time reducing the likelihood that the screw will loosen and pull out, but distribution of the bone cement or fillable material through the screw and throughout the repair site remains a problem. In particular, self-hardening bone cements change viscosity after formulation and the even distribution along the length of the bone screw is challenging for such materials. Another challenge is providing adequate distribution of a bone cement or fillable material while maintaining sufficient screw mechanical strength. Often increasing the number of delivery channels or ports in the screw body can weaken the bone screw. Thus, there remains a need for a cannulated bone screw for use with a bone cement or fillable material that is capable of securing bone at a repair site while also preventing loosening and pull-out of the bone screw following the repair.

SUMMARY OF THE INVENTION

In general, the invention features bone screws, delivery manifolds, kits, and methods of use thereof for the treatment of bone defects.

Accordingly, in a first aspect, the invention features a bone screw (e.g., the bone screw is, or contains, stainless steel alloy, titanium alloy, commercially pure titanium, cobalt chrome, or polyetheretherketone, or combinations thereof) having a length from about 60 millimeters (mm) to 200 mm (e.g., 60 to 130 mm) and including: a cylindrical screw body includes a shaft that defines a longitudinal axis, a screw head at the proximal end of the screw body, and a tip at the distal end of the screw body. The bone screw also includes: an interior channel extending longitudinally through the screw head and through at least a portion of the shaft of the screw body, in which the interior channel has a diameter of about 3 to 5 mm; a first threaded portion on the exterior of the screw head extending from about the proximal end of the screw head along at least a portion of the screw head; a second threaded portion on the exterior of the screw body adjacent to the screw head that extends in a direction along the screw body away from the screw head and having one or more delivery channels; a third threaded portion on the exterior of the screw body adjacent to the tip that extends along a distal portion of the screw body and having one or more delivery channels; a non-threaded portion between the second and third threaded portions on the exterior of the screw body and having one or more delivery channels; and at least first and second helical grooves extending along the exterior of the screw body, in which: the first helical groove is substantially anti-parallel to the second helical groove and the helical grooves extend continuously through the second threaded portion, the non-threaded portion, and at least a portion of the third threaded portion, the delivery channels are coincident with the helical grooves, each of the delivery channels within the helical grooves of the non-threaded portion is separated by a distance of about 18 to 24 mm along the helical groove, and each of the delivery channels of the third threaded portion is separated by a distance of about 5 to 7 mm along the helical groove.

In several embodiments, the bone screw contains one or more, or all, of the following characteristics: each of the delivery channels have a diameter of about 0.5 to 2 mm; the screw head has a length of about 4 to 7 mm and the first threaded portion has a length of about 2 to 4 mm and an exterior diameter of about 6 to 10 mm; the second threaded portion contains about 2 to 4 thread revolutions, 1 to 4 delivery channels and a length of about 5 to 8 mm; the third threaded portion contains about 10 to 20 thread revolutions, 8 to 12 delivery channels and a length of about 25 to 40 mm; the non-threaded portion has a length of about 16 to 86 mm; and/or the ratio of the delivery channels in the third threaded portion to the non-threaded portion is at least 1.25:1.

In still other embodiments, the bone screw contains one or more, or all, of the following characteristics: the interior channel has a diameter of about 3.9 mm; the screw head has a length of about 5.3 mm and the first threaded portion has a length of about 3.2 mm and an exterior diameter of 8.3 mm; the second threaded portion contains about 3 thread revolutions, about 2 delivery channels and a length of about 6.5 mm; the third threaded portion contains about 16 thread revolutions, about 10 delivery channels and a length of about 32 mm and each of the delivery channels of the third threaded portion is separated by a distance of about 6 mm along the helical grooves; the non-threaded portion has a length of about 16 mm to 86 mm and contains at least one to about 24 delivery channels and each of the delivery channels of the non-threaded portion is separated by a distance of about 21 mm along the helical grooves; and/or each of the delivery channels have a diameter of about 1.2 mm.

In several embodiments, the first threaded portion contains about 1 to 5 thread revolutions, the delivery channels are not within about 5 mm of the proximal end and distal end of the bone screw, and the delivery channels are distributed along the helical grooves to provide substantially equal distribution of a flowable medium (e.g., a bone void filler, a cement (e.g., a self-hardening calcium phosphate composition), or a pharmaceutical agent) extruded through each of the delivery channels following introduction of the flowable medium through the screw head into the interior channel. In yet other embodiments, each of the delivery channels is tapered along at least a portion of its radial axis or is substantially cylindrical. In another embodiment, at least one edge of the helical groove(s) contains a self-cutting edge. In still another embodiment, the bone screw has a mean bending stiffness of at least 90-160 N/mm (e.g., 136 N/mm) in a 4-point bend test.

A second aspect of the invention features a bone screw manifold (e.g., which is or contains a polymeric material, such as polypropylene, polyethylene, polystyrene, polytetrafluoroethylene or polyetheretherketone, or combinations thereof) for delivering a fluid to a cannulated and fenestrated bone screw that includes a sheath and a sheath adapter, in which:

a) the sheath contains a cylindrical sheath body that defines a longitudinal axis, a first attachment portion (e.g., the first attachment portion that is sized and shaped to be threadingly engaged with the bone screw head of the bone screw of the first aspect of the invention) at the distal end of the sheath body, a second attachment portion (e.g., the second attachment portion is sized and shaped to be threadingly engaged with a device (e.g., a syringe) for injecting a flowable medium (e.g., a flowable medium that is or contains a bone void filler, a cement, or a pharmaceutical agent)) at the proximal end of the sheath body, and an internal channel having a diameter of at least about 5 mm that extends continuously through the sheath body and through the first and second attachment portions to provide fluid communication through the manifold and in which:
  i) the sheath body has a length of about 60 to 90 mm;
  ii) the first attachment portion contains a threaded region within the internal channel; and
  iii) the second attachment portion contains a threaded region within the internal channel, and contains a first handling portion on the exterior of at least a portion of the second attachment portion; and b) the sheath adapter contains a cylindrical sheath adapter body that defines a longitudinal axis, a third attachment portion at the proximal end of the sheath adapter body, a second handling portion adjacent to the third attachment portion, a fourth attachment portion adjacent to the second handling portion, a tapered portion at the distal end of the sheath adapter body, and an internal channel having a diameter of at least about 2 mm that extends continuously through the sheath adapter body, the third attachment portion, the second handling portion, the fourth attachment portion, and the tapered portion to provide fluid communication through the sheath adapter, in which:
  i) the sheath adapter body has a length of about 50 to 80 mm and an external diameter that is less than the diameter of the internal channel of the sheath;
  ii) the third attachment portion contains a threaded region on an exterior portion thereof;
  iii) the second handling portion contains raised ridges on an exterior portion thereof; and
  iv) the fourth attachment portion contains a threaded region on an exterior portion thereof; and
  in which the sheath adapter body is sized and shaped for insertion into the internal channel of the sheath, the threaded region of the third attachment portion of the sheath adapter is sized and shaped to be threadingly engaged with the threaded region of the second attachment portion of the sheath, thereby reversibly joining the sheath and the sheath adapter when engaged, and, when the sheath and the sheath adapter are joined, the tapered portion of the sheath adapter extends into the first attachment portion of the sheath, and
  in which the manifold is capable of delivering a self-hardening calcium phosphate bone cement to the distal tip of a cannulated and fenestrated bone screw having a length of at least about 130 mm using manual pressure.

In several embodiments of the second aspect of the invention, the bone screw manifold contains one or more, or all, of the following characteristics:

a. the sheath body has an external diameter of at least 8 mm;
b. the first attachment portion has a length of about 5 to 8 mm, the threaded region of the first attachment portion has a length of about 2 to 4 mm and at least 3 thread revolutions, and the internal channel of the first attachment portion has an internal diameter of about 6 to 9 mm;
c. the second attachment portion has a length of about 16 to 24 mm, and in which the threaded region of the second attachment portion has a length of about 4 to 7 mm and at least 2 thread revolutions, and the internal channel of the second attachment portion has an internal diameter of about 5 to 8 mm;
d. the first handling portion includes at least five raised ridges that extend in a direction substantially parallel to the longitudinal axis of the sheath body;
e. the third attachment portion has a length of about 6 to 10 mm and the threaded region of the third attachment portion has a length of about 4 to 7 mm and at least 2 thread revolutions;
f. the second handling portion has a length of about 10 to 15 mm and contains at least four raised ridges on an exterior portion thereof that extend in a direction substantially parallel to the longitudinal axis of the sheath adapter body;
g. the fourth attachment portion has a length of about 6 to 9 mm and the threaded region of the fourth attachment portion has a length of about 3 to 5 mm and at least 2 thread revolutions; and/or
h. the tapered portion has a length of about 5 to 7 mm and an exterior diameter of about 2.5 to 7 mm, and the tapered portion has a chamfer at the distal end.

In still other embodiments of the second aspect of the invention, the bone screw manifold contains one or more, or all, of the following characteristics:

a) the sheath body has a length of about 76.2 mm and the internal channel of the sheath has a diameter of 5.8 mm;
b) the first attachment portion has a length of about 6.4 mm and the threaded region of the first attachment portion has a length of about 3.2 mm, about 3 thread revolutions, and has an internal diameter of about 7.8 mm;
c) the second attachment portion has a length of about 20.4 mm and the threaded region of the second attachment portion has a length of about 5.6 mm, about 2 thread revolutions, and has an internal diameter of about 6.7 mm and contains eight raised ridges;
d) the sheath adapter body has a length of about 67.1 mm and an external diameter of about 5.3 mm and the internal channel of the sheath adapter has a diameter of 2.5 mm;

e) the third attachment portion has a length of about 8.5 mm and the threaded region of the third attachment portion has a length of about 5 mm and about 2 thread revolutions;

f) the second handling portion has a length of about 12.5 mm and contains six raised ridges, g) the fourth attachment portion has a length of about 7.5 mm and the threaded region has a length of about 4.3 mm and about 2 thread revolutions; and/or h) the tapered portion has a length of about 6.1 mm and an exterior diameter of about 3 mm.

In other embodiments of the second aspect of the invention, the threaded region of the second attachment portion has about 2 to 4 thread revolutions, the threaded region of the third attachment portion has about 2 to 4 thread revolutions, and the threaded region of the fourth attachment portion has about 2 to 4 thread revolutions.

A third aspect of the invention features a bone screw washer, which includes i) a cylindrical body includes a shaft that defines a longitudinal axis, in which the body has a length of about 5 to 8 mm and a diameter of 7 to 10.5 mm; ii) a bone engaging portion at the proximal end of the body includes a circumferential lip with a thickness of 1 to 2 mm and a radial diameter of 10 to 15 mm; and iii) a screw head engaging portion at the distal end of the body having a diameter of 6 to 9 mm, in which the diameter of the screw head engaging portion is less than the diameter of the body; and in which the washer is sized and shaped to accept the screw head of the bone screw of the first aspect of the invention and to engage a bone surface. In several embodiments, the washer contains one or more, or all, of the following characteristics:

a) the body has a length of about 6.3 mm and a diameter of 8.6 mm, b) the circumferential lip of the bone engaging portion has a thickness of 1.6 mm and a radial diameter of 12.7 mm, and/or c) the screw head engaging portion has a diameter of 7.5 mm.

In still other embodiments, the washer further contains one or more fenestrations for suture attachment.

A fourth aspect of the invention features a method of treating a patient having a bone defect (e.g., a bone defect that is or that contains a fracture (e.g., a subarticular fracture or a compression fracture), or is a defect of the radius, ulna, fibula, clavicle, humerus, pelvis, femur, patella, tibia, talus, Calcaneus, navicular, cuneiforms, metatarsals, metacarpals, phalanges, scapula, ankle or vertebra), which includes one or more of the following steps of i) positioning the bone screw of the first aspect of the invention in proximity to the bone defect; ii) attaching the sheath of the bone screw manifold of the second aspect of the invention; iii) attaching the sheath adapter of the second aspect of the invention to the sheath; iv) attaching a manual pressure injection device to the fourth attachment portion of the sheath adapter; and v) introducing a flowable medium into the interior channel of the bone screw, whereby the flowable material is extruded through the delivery channels and, upon hardening of the flowable medium, the bone screw is fixed in place, thereby treating the bone defect in the patient.

In several embodiments, the flowable medium is a bone void filler, a cement (e.g., a self-hardening calcium phosphate composition), or a pharmaceutical agent.

In other embodiments, the method further includes, prior to step a), joining the washer of the third aspect of the invention to the screw head, whereby tightening or screwing the bone screw into bone of the patient at or near the fracture provides a compression union that stabilizes the fracture.

A fifth aspect of the invention features a kit, which includes any one or more, or all, of the following: i) the bone screw of the first aspect of the invention; ii) the manifold of the second aspect of the invention; and iii) the washer of the third aspect of the invention. The kit may optionally contain one or more of an injection device, a self-hardening bone cement powder, and instructions for using the kit.

Definitions

As used herein, the term "about" means±10% of the recited value.

By "biocompatible" is meant that the material does not elicit a substantial detrimental response (e.g., an immune response) in the host. It should be appreciated that a foreign object introduced into a living body may induce an immune reaction that will have negative effects on the host. As used herein, the term "biocompatible" is intended to include those materials that may cause some inflammation but does not rise to the level of pathogenesis.

The term "bioresorbable" is meant the ability of a material to be resorbed by the body in vivo. The resorption process involves elimination of the original bioresorbable implant materials through the action of body fluids, enzymes, or cells. "Strongly bioresorbable" means that at least 80% of the total mass of material implanted in vivo is resorbed within one year.

By "bone defect" is meant any bone deficient region, such as a void, gap, recess, or other discontinuity in a bone. A bone defect can be artificially or naturally established, and can occur, for example, due to disease or trauma. Thus, a bone defect can occur as a consequence of pathologic or inflammatory diseases, formation and/or removal of a bone tumor, a surgical intervention, a congenital defect, or a bone fracture, and the like. For example, in the case of certain diseases, such as bone tumors, the bone defect may be artificially established due to removal of the tumor tissue. The bone screws of the invention can be applied, for example, in the repair of periodontal defects, in craniofacial or maxillofacial surgery or reconstruction, in hand surgery, in joint reconstruction, in fracture repair, in orthopedic surgical procedures, and in spinal fusion. The term "bony defect" is also intended to include anatomical sites where augmentation to a bony feature is desired by the patient in the absence of disease or trauma, such as in elective cosmetic surgery. Thus, the "defect" can be one that is subjectively perceived by the patient, and where augmentation of the bone deficient region is desired.

By "bone fill material" or "infill material" is meant any material for infilling a bone that includes an in-situ hardenable material, including, e.g., a flowable medium. The fill material also can include other "fillers," such as filaments, microspheres, powders, granular elements, flakes, chips, tubules and the like, autograft or allograft materials, as well as other chemicals, pharmacological agents, or other bioactive agents.

By "flowable medium" is meant, generally, a formulation of a resorbable or non-resorbable biocompatible agent, e.g., a polymer, such as a thermoset polymer or a thermoplastic polymer, e.g., PMMA (polymethylmethacrylate), a bone void filler material, a cement, or a pharmaceutical agent. In particular, the flowable medium may be a resorbable calcium phosphate or calcium sulphate cement, which is typically self-hardening and, once hardened, may allow for the gradual replacement of the cement with bone. Both resorbable and non-resorbable biocompatible agents, such as bone cements, have been used successfully in the treatment of bone defects.

Preferred calcium phosphate bone cements that can be used with the bone screws of the invention are described in, e.g., U.S. Pat. No. 5,783,217, U.S. Pat. No. 6,027,742, U.S. Pat. No. 6,214,368, U.S. Pat. No. 6,287,341, U.S. Pat. No. 6,331,312, U.S. Pat. No. 6,541,037, U.S. Pat. No. 6,953,594, U.S. Pat. No. 6,972,130, U.S. Pat. No. 7,150,879, U.S. Pat. No. 7,318,841, and U.S. Pat. No. 7,517,539, each of which is incorporated herein by reference, and includes commercially available cements such as BETA-BSM™ injectable paste and CARRIGEN® porous bone substitute material (Etex Corporation, Cambridge, Mass.).

By "major diameter" of a bone screw is meant the longest diameter of the screw body, in a threaded portion, including its threads.

By "minor diameter" of a bone screw is meant the shortest diameter of the screw body, in a threaded portion, including its threads.

By "osteoplasty" is meant any procedure in which bone fill material and/or a flowable medium is delivered into the interior of a bone.

By "self-cutting edge" is meant an edge, flute or angle of a groove or thread of a bone screw that allows the screw to be removed from bone after hardening of the flowable medium that has been extruded from one or more delivery channels (e.g., fenestrations) of the bone screw. Removal of a bone screw having a self-cutting edge may occur without significant torque, e.g. less than 2,500 Newton millimeters (Nmm). A self-cutting edge is active when rotating in the direction where the self-cutting edge is the trailing edge and can scrap material into the groove.

By "treating" or "treatment" is meant the medical management of a patient with the intent that an amelioration, repair, or prevention of an injury or disease, pathological condition, or disorder associated with a bone defect will result. This term includes active treatment, that is, treatment directed specifically toward improvement of the injury or disease, pathological condition, or disorder, and also includes causal treatment, that is, treatment directed toward removal of the cause of the injury or disease, pathological condition, or disorder. In addition, this term includes palliative treatment, that is, treatment designed for the relief of symptoms rather than the curing of the injury or disease, pathological condition, or disorder; preventive treatment, that is, treatment directed to prevention of the injury or disease, pathological condition, or disorder; and supportive treatment, that is, treatment employed to supplement another specific therapy directed toward the improvement of the injury or disease, pathological condition, or disorder.

"Vertebroplasty" includes its ordinary meaning and means any procedure in which fill material is delivered into the interior of a vertebra, e.g., in conjunction with, or using a bone screw of the invention.

Other features and advantages of the invention will be apparent from the following detailed description, and from the claims.

BRIEF DESCRIPTION OF THE DRAWINGS

FIG. 2A is side of the bone screw of FIG. 1, which has been rotated ~180° along the longitudinal axis. FIG. 2B is a cross-sectional view of the bone screw of FIG. 2*a*, as viewed along line A-A in FIG. 2A. FIG. 2C is a cross-sectional view of the bone screw of FIG. 2A, as viewed along line B-B in FIG. 2A.

FIG. 4A is a transparent side view of a bone screw of the invention. Helical grooves on the exterior of the far side of the screw are shown in broken line, while helical grooves on the exterior of the near side of the screw are shown in solid line. FIG. 4B is a cross-sectional view of the bone screw of FIG. 4A, as viewed along line A-A of FIG. 4A.

FIG. 5A is a transparent side view of a bone screw of the invention. Helical grooves on the exterior of the far side of the screw are shown in broken line, while helical grooves on the exterior of the near side of the screw are shown in solid line. FIG. 5B is a cross-sectional view of the bone screw of FIG. 5A, as viewed along line A-A of FIG. 5A.

FIG. 6A is a side view of the sheath. FIG. 6B is a cross-sectional view of the sheath of FIG. 6A, as viewed along line A-A in FIG. 6A. FIG. 6C is an expanded view of region A of FIG. 6B showing the internal threads on the distal end of the sheath. FIG. 6D is an expanded view of region B showing the internal threads of the proximal end of the sheath. FIG. 6E is a cross-sectional view of the sheath of FIG. 6A, as viewed along line B-B in FIG. 6A and showing the raised ridges of the handling portion.

FIGS. 7A-7D are views of a sheath adapter portion of a bone screw manifold of the invention. FIG. 7A is a side view of the sheath adapter. FIG. 7B is a second side view of the sheath adapter. FIG. 7C is a cross-sectional view of the sheath adapter of FIG. 7B, as viewed along line B-B in FIG. 7B and showing the raised ridges of the handling portion.

FIGS. 8A-8C are views of a bone screw washer of the invention. FIG. 8A is a frontal view of the washer. FIG. 8B is a side view of the washer. FIG. 8C is a cross-sectional view of the washer, as viewed along line A-A in FIG. 8A.

FIG. 9A is a depiction of a basic design of the bone void model, in which a syringe is directly attached to a bone screw of the invention. The bone void model does not include a "fracture." The dark area depicts the "bone" into which the screw is inserted. FIG. 9B is a depiction of the bone void model in which a cannula is used as a control. In FIG. 9B, the bone void model has a "fracture" (fracture line shown). A bone screw of the invention is shown for comparison.

FIG. 10A show the bone void model without a "fracture," while FIG. 10B shows the bone void model with a "fracture."

FIG. 11A shows the results of injection of BETA-BSM™ using a bone screw of the invention. FIG.

11B shows the results of injection of BETA-BSM™ using a cannula (control). FIG. 11C shows the results of injection of CARRIGEN™ using a bone screw of the invention. FIG. 11D shows the results of injection of CARRIGEN™ using a cannula (control). The results show that injection of these flowable media through the bone screw produces no signs of voids (light areas), which demonstrates that the bone screws are capable of filling voids in bone.

DETAILED DESCRIPTION OF THE INVENTION

Figure 1:
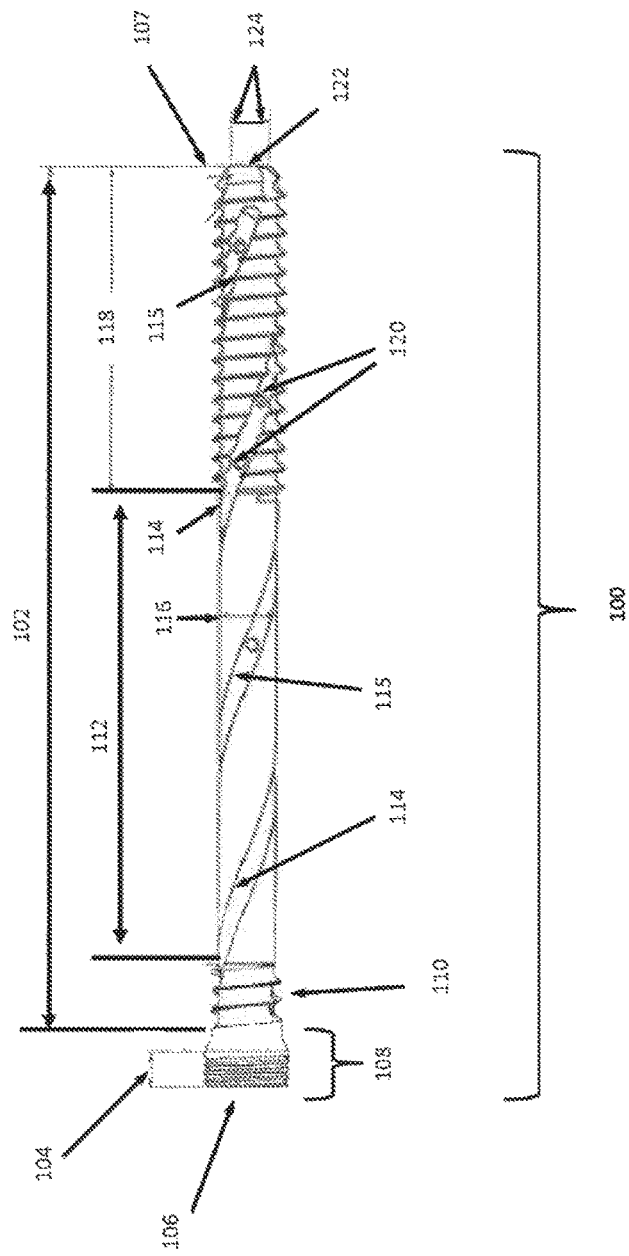
FIG. 1 is a side view of a schematic representation of an embodiment of a bone screw of the invention having first, second, and third threaded portions, a non-threaded portion, and substantially helical exterior grooves that are coincident with a plurality of delivery channels.
Figure 2:
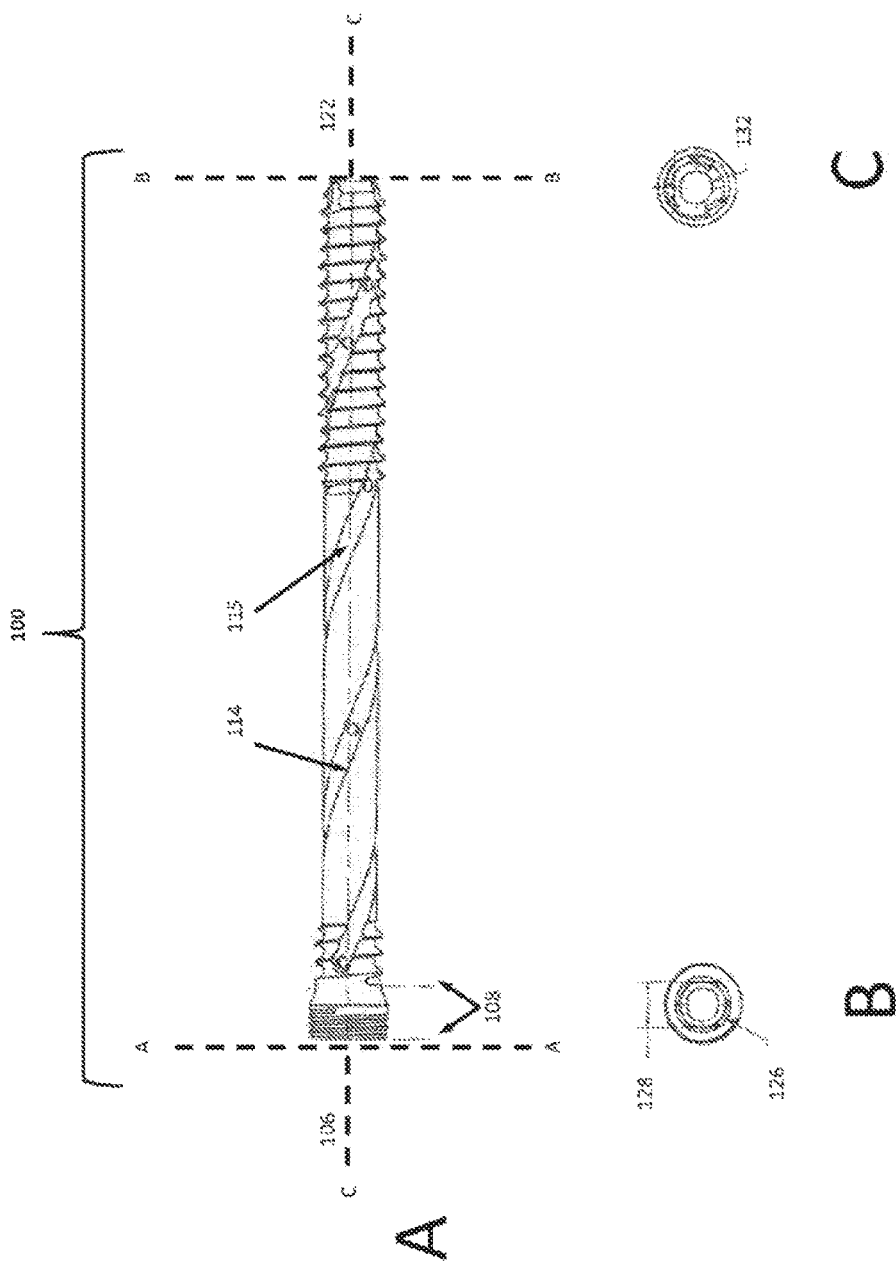
FIGS. 2A-2C are views of a bone screw of the invention.

The invention features bone screws, manifolds, bone screw washers, kits, and methods of treating patients using these devices.

Bone Screws

In particular, bone screws of the invention allow passage of a flowable medium (e.g., a bone cement, such as a resorbable calcium phosphate-based bone cement) through an interior channel of the screws (i.e., a cannula) and extrusion of the flowable medium through a plurality of delivery channels (i.e., fenestrations) that connect the internal channel to the exterior of the screws. Extrusion of the flowable medium to a position around the exterior of bone screws of the invention promotes anchorage of the bone screws in bone after implantation of the screws and upon hardening of the flowable medium. The screws are designed in particular, for fixation of bone fractures using compression. One advantage of bone screws of the invention is that injection of a flowable medium (e.g., a self-hardening calcium phosphate based bone cement) can be achieved using manual pressure (i.e, injection by hand, e.g., using a force of <20 Kgf, such as less than 10 Kgf).

The bone screws are designed to achieve a substantially uniform rate of flow of the flowable medium through substantially all (or at least a plurality of) the delivery channels along the body of the screws with the use of manual pressure and to achieve a substantially uniform distribution of the flowable medium around the exterior surface of the bone screw, thereby anchoring it in the bone. A substantially uniform flow rate of a flowable medium through the delivery channels of the bone screw is achieved by, e.g., varying the number and location of delivery channels along helical exterior grooves (e.g., at least two helical grooves). In particular, the bone screw may have fewer delivery channels at the proximal end than at the distal end. The helical grooves also aid in the distribution of flowable medium to the exterior of the screw, thereby allowing for the medium to flow both axial and radially along the screw in the groove.

Bone screws of the invention have more delivery channels along the exterior groove (e.g., helical groove) in the distal end relative to the proximal end which provides several advantages with respect to the delivery of a flowable medium through and around the cannulated and fenestrated screws. For example, during injection of the flowable material, the material flows from the proximal end of the screw towards the distal end. Extrusion of the flowable medium preferentially out of the proximal most delivery channels, as opposed to equally through the proximal and distal delivery channels, results in voids of bone cement around the bone screw. The bone screw of the invention achieves substantially uniform distribution of the flowable medium along the entire longitudinal axis by reducing the number of and increasing the spacing of the delivery channels at the proximal end of the screw shaft, thereby promoting delivery of the flowable material along the entire length of the screw, including to the distal end of the screw. Increasing the number of delivery channels at the distal end, relative to the proximal end of the bone screw shaft also results in a reduction of the resistance of the flow of a flowable medium along the entire length of the bone screws, including the distal end. The inventive screw solves this problem by having a larger number of delivery channels at the distal end, thus reducing the resistance to flow.

The reduction in flow resistance at the distal end of the screw provides another important benefit; the flowable medium can be injected into the screw of the invention using manual pressure. In this context, manual pressure includes any method of injecting a flowable medium (e.g., an injectable self-hardening calcium phosphate bone paste) by hand (i.e., without the aid of a mechanical, electrical, or motorized pump or hydraulic) into the bone screw of the invention. This improves the ease of use of the bone screw and minimizes the risk of any potential over-pressurization of the flowable medium during screw installation. The manifold of the invention provides an effective and stable way to provide a flowable medium to the bone screw interior channel. The use of manual pressure is greatly simplified by the use of a sheath and sheath adapter, which combine to produce the manifold and create a reliable and efficient system for transferring the flowable material into the bone screw.

The bone screws of the invention also exhibit improved mechanical properties and help avoid a loss of mechanical integrity of the screw, which can result in a number of medical complications. For example, the length of the bone screw is increased by varying the length of the non-threaded portion of the screw. This portion of the screw has fewer delivery channels, which provides additional strength to the screw.

The bone screws of the invention also include two antiparallel helical grooves that, in combination with an asymmetric distribution of delivery channels along the screw body, provide a mechanically strong, highly efficient bone screw for use with flowable medium at manual pressures.

The bone screws of the invention can be used even with bones of reduced quality (e.g., osteoporotic bone) or in revision surgeries (e.g., they can be used to replaced previously inserted bone screws).

The bone screws of the invention can be used, for example, in osteosynthesis to internally stabilize and/or join bones, e.g., fractured (broken) bones, either in conjunction with other mechanical devices, such as metal plates, pins, rods, or wires, or individually. Without limitation, the bone screws of the invention can be used as, e.g., small fragment screws, cortex screws, cancellous screws, dynamic hip screws, lag screws, non-self-tapping and self-tapping screws, and malleolar screws. The size and function of the bone screw of the invention may vary depending on its intended use (e.g., depending on the length necessary to provide fixation in the cortex of a longe bone above and below a fracture). The head of the bone screw may be modified in order to operate with any of a number of appropriate drivers and drills known in the art (e.g., Robertson driver, a slotted driver, a Phillips driver, a Torx driver, a triple square driver, a polydrive driver, a one-way clutch driver, a spline drive driver, a double hex driver, or a Bristol driver).

Structure

Referring to FIGS. 1 to 5, bone screw 100 includes threaded screw body 102 and screw head 108 attached to one end of screw body 102, and tip 122. Bone screw 100 includes proximal end 106, which defines the end of the bone screw accessible during installation of the screw, and distal end 107 is defines the end of the bone screw that enters the bone first during installation. Bone screw 100 further includes interior channel 124 extending longitudinally through screw head 108 and through screw body 102. Bone screw 100 includes three threaded portions. First threaded portion 104 is located on the exterior of the screw head 108. Second threaded portion 110 is located adjacent to the screw head 108. Third threaded portion 118 is located adjacent to distal tip 122. Second and third threaded portions are separated by non-threaded portion 112. Bone screw 100 also includes two helical grooves 114, 115, which extend continuously through portions of 110, 112, and 118. Helical grooves 114, 115 are substantially anti-parallel and have a periodicity such that the two helical grooves do not overlap with each other. Other configurations may be employed for the exterior grooves (e.g., semi-parallel, parallel, oscillating, overlapping). Coincident with helical grooves 114, 115 are a plurality of delivery channels 120 (two representative delivery channels are identified by the arrows in FIG. 1).

Bone screw 100 may have a length in the range of about 60 mm to 200 mm, e.g., about 60 mm, 65 mm, 70 mm, 75 mm, 80 mm, 85 mm, 90 mm, 95 mm, 100 mm, 105 mm, 110 mm, 115 mm, 120 mm, 125 mm, 130 mm, 140 mm, 150 mm, 160 mm, 170 mm, 180 mm, 190 mm, or 200 mm, or a value in a range spanning any of the preceeding values. A preferred bone screw of the invention may have length of about 60 mm to 130 mm. Bone screw 100 has exterior diameter 116 of about 4 mm to 7 mm, e.g., about 4 mm, 4.5 mm, 5 mm, 5.5 mm, 6 mm, 6.5 mm, or 7 mm or a value in a range spanning any of the preceeding values, and preferably 5.7 mm (see FIGS. 1 and 4B).

Screw head 108 may have a length of about 4 mm to 7 mm, e.g., about 4 mm, 5 mm, 6 mm, and 7 mm, or a value in a range spanning any of the preceeding values. In a preferred embodiment bone screw 100 has a screw head length of about 5.3 mm. Screw head 108 may have an external diameter in a range of about 6.5 mm to 9.5 mm, e.g., about 6.5 mm, 7 mm, 7.5 mm, 8 mm, 8.5 mm, 9 mm, and 9.5 mm, or a value in a range spanning any of the preceeding values. In a preferred embodiment the screw head length is about 8.3 mm. The screw head has hexagonal opening 128 (see FIG. 2B) with a width in the range of about 4 mm to 6 mm, e.g., about 4 mm, 4.5 mm, 5 mm, 5.5 mm or 6 mm, or a value in a range spanning any of the preceeding values, and preferably about 4.76 mm.

Tip 122 of bone screw 100 may have internal diameter 132 in a range of about 3 mm to 3.8 mm, e.g., about 3.0, 3.2, 3.4, 3.6, or 3.8 mm, or a value in a range spanning any of the preceeding values, and preferably about 3.4 mm (see FIG. 1C).

Interior channel 124 has a diameter in the range of about 3 mm to 5 mm, e.g., about 3 mm, 3.5 mm, 4 mm, 4.5 mm, and 5 mm, or a value in a range spanning any of the preceeding values (FIG. 1). In a preferred embodiment, interior channel 124 has a length of about 3.9 mm.

First threaded portion 104 has a length in the range of about 2 mm to 5 mm, e.g., about 2 mm, 2.5 mm, 3 mm, 3.5 mm, 4 mm, 4.5 mm, 5 mm, or a value in a range spanning any of the preceeding values, and preferably about 3.5 mm. First threaded portion 104 may have 1, 2, 3, or 4 thread revolutions, most preferably about 3 thread revolutions. Screw threads of first threaded portion 104 may have a major diameter 136 in the range of about 7.9 mm to 8.7 mm, e.g., about 7.9, 8.1, 7.0, 8.5, or 8.7 mm, or a value in a range spanning any of the preceeding values, and preferably 8.3 mm (see FIG. 3). Screw threads of first threaded portion 104 may have a minor diameter 134 in the range of about 7.3 mm to 7.9 mm, e.g., about 7.3, 7.5, 7.7, 7.9, or 8.1 mm, or a value in a range spanning any of the preceeding values, and preferably about 7.7 mm. Screw threads of first threaded portion 104 may have a thread thickness 138 in the range of about 0.1 mm to 0.5 mm, e.g., about 0.1, 0.2, 0.3, 04, or 0.5 mm, or a value in a range spanning any of the preceeding values, and preferably about 0.3 mm. Screw threads of first threaded portion 104 may have a thread spacing 140 in a range of about 0.5 mm to 1.1 mm, e.g., about 0.5, 0.6, 07, 0.8, 0.9, 1.0, or 1.1 mm, or a value in a range spanning any of the preceeding values, and preferably about 0.8 mm.

Second threaded portion 110 may have a length in a range of about 3 mm to 9 mm, e.g., about 3 mm, 4 mm, 5.6 mm, 7 mm or 9 mm, or a value in a range spanning any of the preceeding values. In a preferred embodiment, the has a screw head length has a of about 5.6 mm. Screw threads of second threaded portion 110 may have a major diameter in a range of about 6.0 mm to 8.0 mm, e.g., about 6.0, 6.5, 7, 7.5, or 8 mm, or a value in a range spanning any of the preceeding values, and preferably about 7 mm. Screw threads of second threaded portion 110 may have a minor diameter in the range of about 5.4 mm to 6.5 mm, e.g., about 5.4.5, 5.0, 5.5, 6.0, or 6.5 mm, or a value in a range spanning any of the preceeding values, and preferably about 5.4 mm. Screw threads of second threaded portion 110 may have a thread thickness in a range of about 0.05 mm to 0.35 mm, e.g., about 0.05, 0.1, 0.15, 0.2, 0.25, 0.3, or 0.35 mm, or a value in a range spanning any of the preceeding values, and preferably about 0.2 mm. Screw threads of the second threaded portion 110 may have a thread spacing in a range of about 1.6 mm to 2.2 mm, e.g., about 1.6, 1.7, 1.8, 1.9, 2.0, 2.1, or 2.2 mm, or a value in a range spanning any of the preceeding values, and preferably about 1.9 mm. The second threaded portion may have 1, 2, 3, or 4 thread revolutions, and preferably about 2 thread revolutions.

Figure 3:
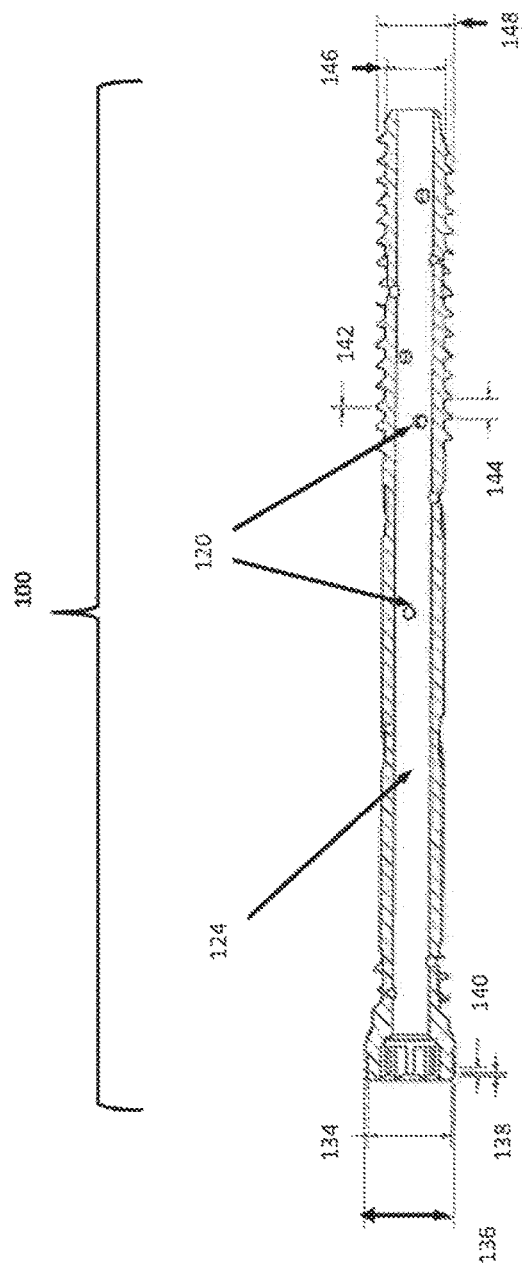
FIG. 3 is a cross-sectional view of a bone screw of the invention, as viewed along line A-A of FIG. 3.
Figure 4:
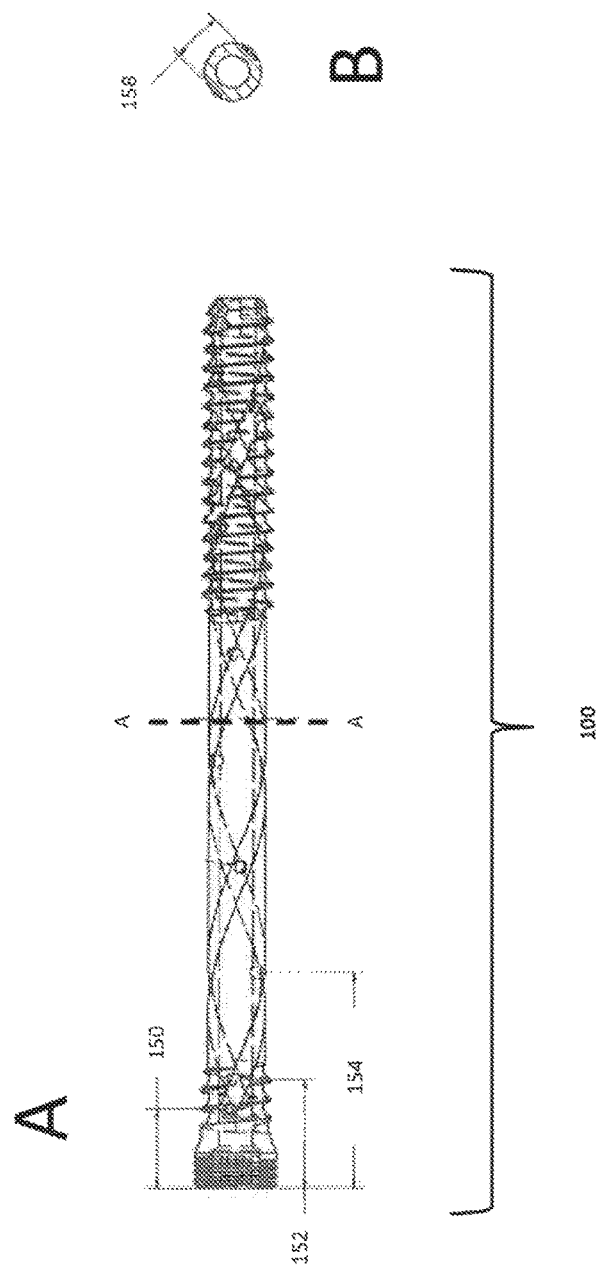
FIGS. 4A and 4B are views of a bone screw of the invention.
Figure 5:
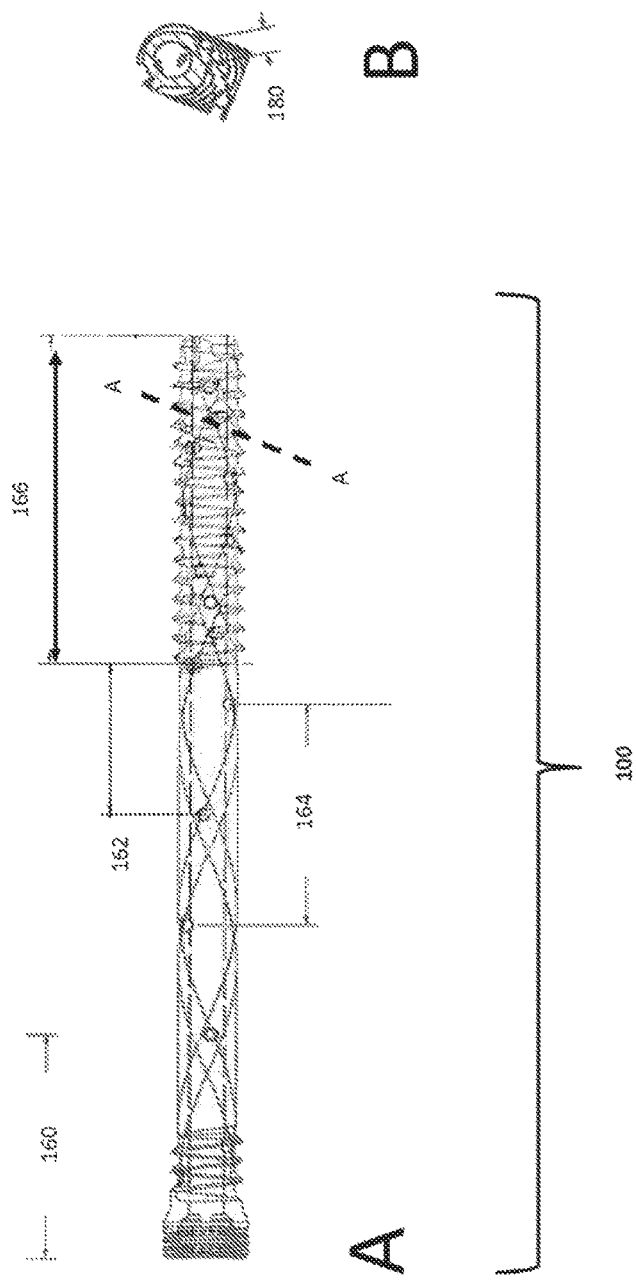
FIGS. 5A and 5B are views of a bone screw of the invention.

Third threaded portion 118 may have a length in the range of about 26 mm to 38 mm, e.g., about 26 mm, 28 mm, 30 mm, 32 mm, 34 mm, 36 mm, or 38 mm, and preferably about 32 mm. Third threaded portion 118 may have thread revolutions in a range of about 10 to 22, e.g., about 10, 12, 14, 16, 18, 20, or 22 thread revolutions, or a value in a range spanning any of the preceeding values, and preferably about 16 thread revolutions. Third threaded portion 118 may have delivery channels in a range of about 8 to 12 delivery channels, e.g., about 8, 9, 10, 11, or 12 delivery channels, and preferrably 10 delivery channels each of which is preferably coincident with an exterior helical groove. Screw threads of third threaded portion 118 may have a major diameter 148 in a range of about 6 mm to 8 mm, e.g., about 6.0, 6.5, 7, 7.5, or 8 mm, or a value in a range spanning any of the preceeding values, and preferably about 7 mm. Screw threads of third threaded portion 118 may have a minor diameter 146 in a range of about 5.4 mm to 6.5 mm, e.g., about 5.4.5, 5.0, 5.5, 6.0, or 6.5 mm, or a value in a range spanning any of the preceeding values, and preferably about 5.4 mm (FIG. 3). Screw threads of third threaded portion 118 may have a thread thickness 142 in a range of about 0.05 mm to 0.35 mm, e.g., about 0.05, 0.1, 0.15, 0.2, 0.25, 0.3, or 0.35 mm, or a value in a range spanning any of the preceeding values, and preferably about 0.2 mm. Screw threads of third threaded portion 118 may have thread spacing 144 in a range of about 1.6 mm to 1.9 mm, e.g., about 1.6, 1.7, 1.8, 1.9, 2.0, 2.1, or 2.2 mm, or a value in a range spanning any of the preceeding values, and preferably about 1.9 mm (FIG. 3).

Bone screw 100 has non-threaded portion 112 that may have a length in the range of about 16 mm to 86 mm, e.g., 16 mm, 32 mm, 48 mm, 64 mm, 80 mm, and 86 mm, or a value in a range spanning any of the preceeding values. Non-threaded portion 112 may have about 2 delivery channels for about every 21 mm length of helical groove 114, 115.

Delivery channels 120 may have a diameter of about 0.5 to 2 mm, preferably about 1.2 mm. The delivery channels are coincident with the anti-parallel substantially helical grooves 114, 115. Delivery channel 120 may have a spacing along the helical groove(s) of between 5 to 7 mm within third threaded portion 118 and may have a spacing within non-threaded portion 112 of between 18 to 24 mm. Preferably, delivery channels 120 in third threaded portion 118 have a separation of about 6 mm along the helical grooves 114, 115. Preferably, delivery channels 120 in non-threaded portion 112 have a separation of about 21 mm along the helical grooves 114, 115.

The bone screw tip 122 can provide a self-tapping configuration (see FIG. 2C).

Functional Design

The length of a bone screw of the invention may varied by increasing the length of non-threaded portion 112 (see FIG. 1), while the lengths of second and third threaded portions, 110 and 118, may remain constant (see, FIG. 1).

Bone screw 100 contains screw head 108 with first threaded portion 104, second threaded portion 110, non-threaded portion 112, third threaded portion 118, interior channel 124 and tip 122 (see FIG. 1). Screw body 102 of bone screw 100 also contains two substantially, anti-parallel helical exterior grooves 114 connecting delivery channels 120 to the exterior of the screw body.

Figure 6:
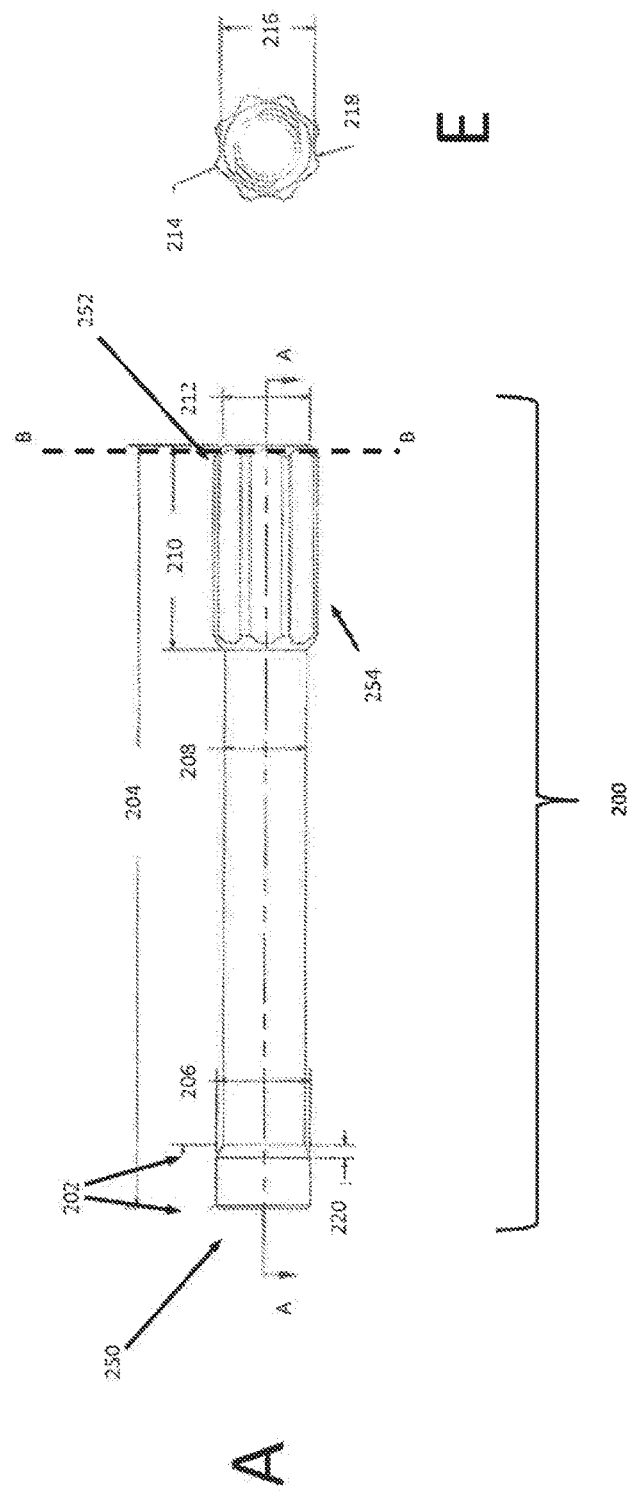
FIGS. 6A-6E are views of a sheath portion of a bone screw manifold of the invention.

Screw head 108 is circular and includes screw head threads 104 on its exterior (FIG. 1), to which, e.g., sheath 200 of a delivery manifold of the invention may be attached. In particular, first attachment portion 202 of sheath 200 is sized and shaped to engage screw head threads 104 of bone screw 100 (FIG. 6). Screw head 108 additionally contains hexagonal opening 128 internal to screw head 108, viewed in FIG. 2B from proximal end 106, in which a rotational driver may be inserted. Opening 128 for coupling a driver can have other shapes, such as a hexagonal shape, square shape, pentagonal shape, diamond shape, etc., that allow mating of a driver or other instrument to screw head 108. Screw head 108 can provide a self-tapping configuration (see FIGS. 2A and 2B).

For example, screw head 108 may be shaped for engagement with, and driven by, a variety of drivers, such as a Robertson driver, a slotted driver, a Phillips driver, a Torx driver, a triple square driver, a polydrive driver, a one-way clutch driver, a spline drive driver, a double hex driver, or a Bristol driver. Rotational drivers may turn clockwise or counter-clockwise (depending on the thread direction) to tighten a bone screw into final or near-final position.

Interior channel 124 (FIG. 1) may have a diameter that facilitates the transfer and delivery of a flowable medium, such as a bone void filler, cement, or pharmaceutical agent substantially throughout the length of a bone screw and through tip 122 when bone screw 100 is fully cannulated.

First threaded portion 108 allows for the attachment of a manifold or other threaded device to proximal end of the bone screw 106 of the bone screw 100 (FIG. 1). Second threaded portion 110 allows for anchoring of the proximal end bone screw 100 into bone. A portion of at least one exterior groove (e.g., exterior helical groove 114, 115) may extend into second threaded portion 110. Also, second threaded portion 110 may have one or more delivery channels coincident with the exterior groove(s). In one embodiment, second threaded portion 110 has a length of 8.5 mm, about three thread revolutions and at least 1 delivery channel coincident with a first exterior helical groove 114 and at least 1 delivery channel coincident with a second helical groove 115.

Third threaded portion 118 is adjacent to tip 122 at distal end 107 of bone screw 100. Third threaded portion 118 contains a portion of at least one, and preferably at least two, exterior grooves (e.g, at least a portion of substantially anti-parallel exterior grooves 114 and 115). Third threaded portion may have one or more delivery channels 120 coincident with the exterior groove(s). Third threaded portion has more delivery channels, e.g., a ratio of at least about 1.25:1, than the two more proximal portions: the non-threaded and second threaded portions.

The length of bone screw 100 may be increased or decreased by increasing or decreasing, e.g., the length of non-threaded portion 112. Non-threaded portion 112 is designed with fewer delivery channels relative to the third threaded portion 118 in order to facilitate the flow of a flowable medium to the distal end of bone screw 100 and to promote a substantially uniform delivery of the flowable medium around the exterior of the bone screw. The ratio of the delivery channels in non-threaded portion 112 to the third threaded portion 118 depends on the length of both portions. For example, if third threaded portion 118 has a length of 32 mm and a spacing of delivery channels about every 6 mm, then the ratio of delivery channels in third threaded portion 118 to non-threaded portion 112 ranges from about 6.7:1 to 1.25:1 for screws up to about 130 mm in length.

Exterior grooves 114, 115 are substantially helical and anti-parallel. Exterior grooves 114, 115 are coincident with delivery channels 120. Exterior grooves 114, 115 provide a path for a flowable medium to move around the exterior of bone screw 100. Exterior grooves 114, 115 may have a periodicity of about 50.8 mm. In some embodiments, bone screw 100 may have one 114 or two 114, 115 external grooves or more (e.g., more than three external grooves). Also exterior grooves of bone screw 100 may be parallel, anti-parallel, semi-parallel, oscillating, or overlapping.

Delivery channels 120 allow for a flowable medium to be distributed to the exterior of bone screw 100. Delivery channels 120 are coincident with exterior grooves 114, 115. Third threaded region 118 has more delivery channels 120 than non-threaded portion 112 and second threaded portion 110. In general, the ratio of delivery channels in third threaded portion 118 to non-threaded portion 112 is at least 1.25:1 (e.g., at least 2:1). In one embodiment, third threaded portion 118 has ten delivery channels (5 in each helical groove in the third threaded portion 118), second threaded portion 110 has 2 delivery channels (1 in each helical groove), and non-threaded portion 112 has a length of about 86 mm (for a full screw body length of 130 mm) and 8 delivery channels (4 delivery channels in each groove). This configuration achieves a substantially uniform flow rate of a flowable medium through delivery channels 120. In this configuration, the distance 150 from proximal end 106 of bone screw 100 to the first delivery channel in second threaded portion 110 is about 8 mm. The distance from proximal end 106 of bone screw 100 and the first delivery channel in non-threaded portion 112 is about 16.5 mm.

Bone screw tip 122 can provide a self-tapping configuration (see FIG. 2C). A self-tapping configuration allows for easier entry into the bone and more efficient installation.

Bone Screw Manifolds

The invention also features a manifold which, in combination with the bone screw, provides efficient and effective transfer of a flowable medium into the bone screw. The bone screw manifold of the invention is formed of two parts: a sheath and a sheath adapter. Sheaths of the invention are cylindrical bodies with attachment portions on both the distal and proximal ends (i.e., first and second attachment portions, respectively). The first attachment portion of the sheath attaches to the bone screw head, while the second attachment portion attaches to the sheath adapter. Sheath adapters of the invention are cylindrical bodies with two attachment portions: a third attachment portion that connects the sheath adapter to the sheath and a fourth attachment portion that attaches the sheath adapter to an injection device.

Manifolds of the invention have several advantages. The sheath portion of the manifold provides a guiding cylindrical body for accessing the screw head of the bone screw. The sheath can act like a guidewire during bone repair surgical procedures by assisting the surgeon to locate the screw head (e.g., for contact with a rotational driver or other instrument, as well as with the sheath adapter). The sheath also provides a stable anchoring point for the sheath adapter, thereby making the process of injecting the flowable medium more efficient. Sheath adapters of the invention provide a reduced manifold volume for injection because the internal channel of the sheath adapter can be smaller than a single manifold design in which the sheath internal diameter is similar to the screw head diameter. Sheath adapters of the invention also provide a seal for injecting the flowable medium within the bone screw head, thereby isolating the flowable medium from the sheath and preventing the sheath from filling with the flowable medium, which can make accessing the screw head more difficult.

Structure

Referring to FIGS. 6 and 7, sheath 200 (FIG. 6) and sheath adapter 300 (FIG. 7) are used in combination to form a delivery manifold of the invention, which facilitates introduction of a flowable medium into a cannulated and fenestrated bone screw (e.g., a bone screw of the invention, such as bone screw 100 of FIGS. 1-5). Attachment of sheath 200 to screw head 108 of bone screw 100 provides a channel for insertion and stabilization of the sheath adapter 300. Sheath 200 has a cylindrical body 204 and distal end 250 containing first attachment portion 202 for attachment to bone screw 100 (FIG. 6A). Sheath 200 has second attachment portion 210 at proximal end 252 of cylindrical body 204 for attachment to sheath adapter 300 (FIG. 6A). A series of raised ridges 218 (FIG. 6E) comprising first handling portion 254 (FIG. 6A) can be located on the outside of second attachment portion 210 (side view in FIG. 6A, view down longitudinal axis in FIG. 6E).

Sheath adapter 300 has cylindrical body 344, (FIG. 7B), and tapered portion 304 (FIG. 7A) and fluid communication channel 356 (internal channel; Fig. &C), for conveying a flowable medium into bone screw 100. Tapered portion 304 is adjacent distal end 346. Sheath adapter 300 has third attachment portion 326 (FIG. 7B) that is shaped and sized to be reversibly, threadingly engaged with second attachment portion 232 of sheath 200. Second handling portion 352 is adjacent to third attachment portion 326 and includes at least 4 raised ridges that facilitate handling and tightening to sheath 200 during installation of bone screw 100. Adjacent to second handling portion 352 is fourth attachment portion 318 (Fig. &A) adjacent to proximal end 348.

Sheath cylindrical body 204 defines a longitudinal axis and has a length of about 60 mm to 90 mm, exterior diameter 208 of at least about 8 mm, and interior channel 256 with a diameter 230 of 5.7 mm (see, FIGS. 6A and 6B).

Sheath first attachment portion 202 is (FIG. 6A) located at the distal end of sheath body 204 and has a length of about 5 mm to 8 mm, and internal threaded region 222 (FIG. 6B) with an interior diameter of about 6 mm to 9 mm. Threaded region 222 of first attachment portion 202 may have thread thickness 240 of about 0.3 mm and thread spacing 242 of about 0.8 mm (see FIG. 6C).

Second attachment portion 210 (FIG. 6A) may have a length of about 16 to 24 mm, preferably about 20.4 mm. Threaded region 234 (FIG. 6B) may have a length of about 5.6 mm, about 2 thread revolutions, and a thread thickness 246 of about 0.7 mm and a thread spacing 244 of about 1.5 mm to 2.5 mm (see FIG. 6D). Threaded region 234 of second attachment portion 210 is within internal channel 256 (FIG. 6B) and may have a diameter of about 6.7 mm. Sheath first handling portion 254 is on the exterior of the second attachment portion 210.

First handling portion 254 (FIG. 6A) has about 8 raised ridges 218 (FIG. 6E) which are substantially parallel to cylindrical body 204 of sheath 200. First handling portion 254 may have a length of about 16 mm to 24 mm, preferably about 20.4 mm.

Sheath adapter cylindrical body 344 (FIG. 7B) defines a longitudinal axis and may have a length of about 50 to 80 mm. Cylindrical body 344 of sheath adapter 300 may have an exterior diameter of about 4 to 7 mm. Internal channel 356 (FIG. 7C) may have a diameter of about 1 mm to 3 mm. Cylindrical body 344 may have a length of about 50 mm to 80 mm, or a value in a range spanning any of the preceeding values, preferably about 67.1 mm.

Sheath adapter third attachment portion 326 (FIG. 7B) at proximal end 350 of sheath adapter cylindrical body, may have a length of about 6 mm to 10 mm and contains exterior threaded portion 354 with a length of about 4 mm to 7 mm and at least 2 thread revolutions.

Sheath adapter second handling portion 352 is adjacent to the third attachment portion 326. Second handling region 352 has a length of about 10 mm to 15 mm and has at least four (e.g., 4, 5, or 6) raised ridges on an exterior portion thereof.

Sheath adapter fourth attachment portion 318 (FIG. 7A) is adjacent to second handling portion 352 and is located at the proximal end of sheath adapter 300. Fourth attachment portion 318 may have a length of about 3 mm to 5 mm and has an exterior threaded portion 328 (FIG. 7B) that may have at least 2 thread revolutions.

Sheath adapter tapered portion 304 (FIG. 7A) is located at the end of the distal end of the sheath adapter body. Tapered portion 304 may have a length of about 5 mm to 7 mm and an exterior diameter of about 2.5 mm to 7 mm. Tapered portion may have a chamfer at the distal end.

Functional Design

First attachment portion 202 of sheath 200 is sized and shaped to be threadingly engaged to bone screw 100 (see FIG. 6). Sheath 200 provides a conduit for, and stabilizes, sheath adapter 300 and provides a stable manifold for sealing tapered portion 304 of sheath adapter 300 with interior channel 124 of bone screw 100.

Second attachment portion 210 of sheath 200 is located at proximal end 252 and provides a threaded region 234 (FIG. 6B) for threadingly engaging with third attachment portion 326 of the sheath adapter 300, thereby reversibly lockingly coupling sheath 200 to sheath adapter 300 (see FIGS. 6-7). Once the sheath adapter has been secured to the sheath, the tapered portion of the sheath adapter is sealed into the interior channel of bone screw 100.

First handling portion 254 has a plurality of raises ridges 218 (FIG. 6E) that are substantially parallel to cylindrical body 204 of sheath 200. First handling portion 250 facilitates the attachment of the sheath 200 onto bone screw head 108 by making cylindrical body 204 easier to grip and turn.

Cylindrical body 302 has distal 346 and proximal 348 ends: distal end 346 has tapered end 304 that seals into bone screw interior channel 124 when sheath 200 and sheath adapter 300 are engaged, which allows for transfer of a flowable medium from an injection device into bone screw 100.

Third attachment portion 326 of sheath adapter 300 is at proximal end 350 of the sheath adapter cylindrical body. The third attachment portion threadingly engages the second attachment portion 210 of the sheath 200 to form a reversible union between the sheath and the sheath adapter.

Second handling portion 352 of sheath adapter 300 assists in the coupling of third attachment portion 326 to second attachment portion 210, thus easing the joining the sheath and sheath adapter by hand. Second handling portion allows for easy installation or removal of the sheath adapter, thereby improving the efficiency of bone defect repair.

Fourth attachment portion 318 of sheath adapter 300 is adjacent to second handling portion 352 and located at proximal end 348 of sheath adapter 300. Fourth attachment portion 318 has threads 328 sized and shaped to engage an injection device, such as a syringe. Threads 328 can be in the form of, e.g., a Luer lock. Fourth attachment portion 318 may have threads 328 to facilitate coupling to other injection devices.

Sheath adapter tapered portion 304 is location at distal end 346 of sheath adapter 300. Tapered portion 304 may have a tapered diameter and a chamfered end to allow the joining and sealing of sheath adapter 300 into screw head 108 producing a continuous interior channel by the combination of interior channels of the bone screw 124 and internal channel 356 of sheath adapter 300.

Bone Screw Washers

The invention also includes a washer for use with the bone screw of the invention. The combination of a mechanically strong fenestrated screw with a washer allows for compression applications in the treatment and repair of a large range of bone defects and fractures, e.g., fractures that require compression. The bone screw washers have a proximal end with a circumferential lip, a cylindrical body, and a distal end with a diameter restriction.

Structure

Referring to FIG. 8, bone screw washer 400 has cylindrical body 430 that defines a longitudinal axis or shaft having outer diameter 418 of about 7 to 12 mm (FIG. 8c), a length of about 5 to 8 mm and internal diameter 404 of about 7 to 10.5 mm. Washer 400 has proximal end 422 and distal end 424 (FIG. 8C). Distal end 424 has radial constriction 406 that facilitates engagement of washer 400 with bone screw 100. Radial constriction 406 has an internal diameter of about 6 to 9 mm. Washer 400 has circumferential lip 412 that engages the exterior surface of bone when used with a bone screw, e.g., bone screw 100 (see FIGS. 8A, 8C). Circumferential lip 412 extends radially outward from body 430 (FIG. 8C) to engage a bone surface and to facilitate compression when used in fracture fixation. Circumferential lip 412 has a diameter of about 10 to 15 mm and a thickness of about 1 to 2 mm. Proximal end 422 of washer 400 is sized and shaped to allow for insertion of, and engagement with, a bone screw (e.g., bone screw 100 of FIGS. 1-5). Opening 402 of washer 400 has a diameter of about 7.5 to 12 mm. Bone screw washer 400 may have fenestrations (e.g. on the circumferential lip 412) that facilitate suture attachment for securing ligaments and tendons.

Functional Design

Figure 16:
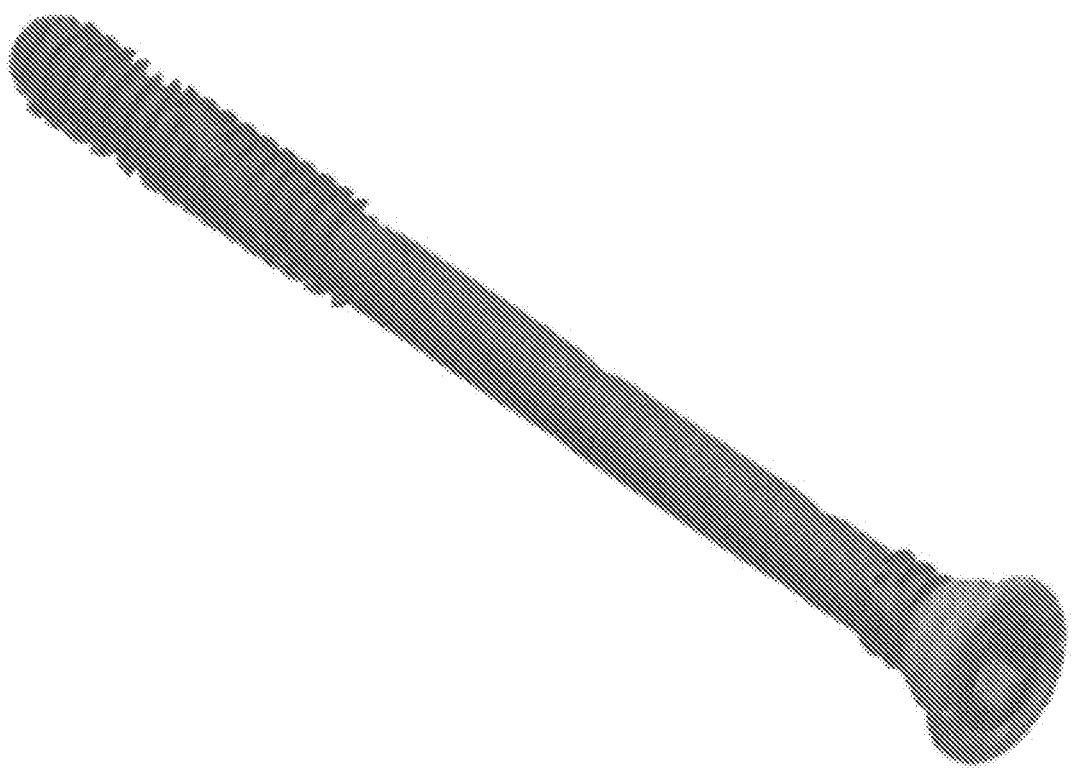
FIG. 16 is a side view of a bone screw of the invention engaged with a washer of the invention (covering the screw head). The washer also includes two fenestrations that permit suture attachment from the washer to adjacent tissues (e.g., bone or soft tissues).
Figure 17:
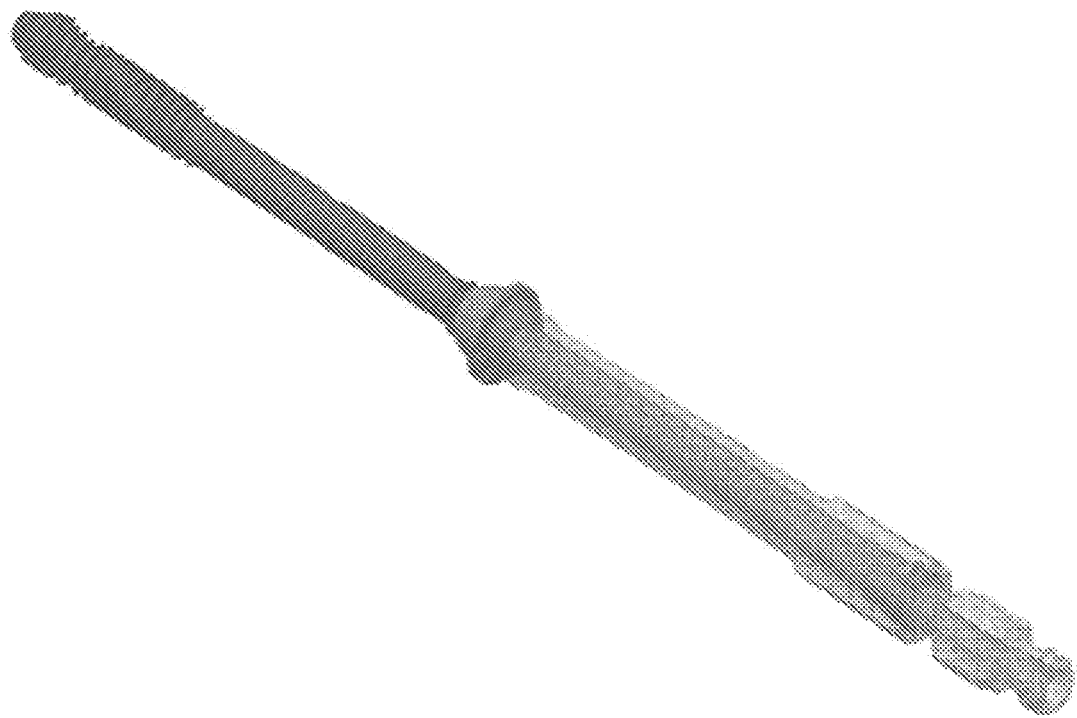
FIG. 17 is a side view of the bone screw and washer of FIG. 16 engaged with a delivery manifold (sheath+sheath adapter) of the invention.

Bone screw washer 400 (FIG. 8) is sized and shaped to accept bone screw head 108 of bone screw 100 by passing the distal end 107 of bone screw 100 through proximal end 422 and into shaft 404. Bone screw 100 is conveyed through washer 400 until screw head 108 engages distal constriction 406 of bone screw washer 400 (see FIGS. 16 and 17, showing assembly of bone screw and washer). Bone screw washer 400 contains proximal opening 402 that allows screw head 108 to fit inside washer 400, such that screw head 108 does not extend substantially above the surface of proximal opening 402 when used in compression fixation (see FIG. 16). During injection of a flowable medium into bone screw 100, e.g., using a manifold of the invention, washer 400 can be moved towards the distal end of bone screw 100 to provide access to the threads of first attachment portion 108 by sheath 200 (see FIG. 17).

Methods of Treatment Using a Bone Screw of the Invention

The bone screws of the invention may be used to treat a bone defect in a patient in need thereof. In particular, the bone screws of the invention, when used with a bone screw washer, such as the washer of the invention, can be used to provide compressive fixation in a patient with a fracture requiring compression.

Particular bone defects that may be treated using the bone screws of the invention include, e.g., any bone deficient region, such as a void, gap, recess, or other discontinuity in a bone. The bone defect may be due to, for example, disease or trauma. The bone screws of the invention can be applied, for example, in the repair of periodontal defects, in craniofacial or maxillofacial surgery or reconstruction, in hand surgery, in joint reconstruction, in fracture repair, in orthopedic surgical procedures, and in spinal fusion. The bone screws of the invention may also be used, for example, in osteosynthesis to internally stabilize and/or join bones, e.g., fractured (broken) bones, either in conjunction with other mechanical devices, such as washers (e.g., a washer of the invention), metal plates, pins, rods, or wires, or individually. For example, the bone screws of the invention can be used with a bone screw washer (e.g., a washer of the invention) to provide compressive fixation of bone defects and bone fractures. In particular, the bone screws are useful for the treatment of defects or breaks in large bones. Non-limiting examples of bone fractures include, e.g., stable fractures, transverse fractures, oblique fractures, spiral fractures, comminuted fractures and open and displaced fractures. Exemplary large bones that may require fracture fixation include, e.g., the femur, tibia, fibula, humerus, ulna, radius, $7^{th}$ and $8^{th}$ ribs, innominate bone (hip bone) and sternum.

The method of treating a patient having a bone defect (e.g., subarticular fracture, a defect of the spine or vertebra, or a defect of the radius, ulna, fibula, clavicle, humerus, pelvis, femur, patella, tibia, talus, calcaneus, navicular, cuneiforms, metatarsals, metacarpals, phalanges, scapula, ankle, teeth, or mandible) includes the following: a) positioning the bone screw of the invention in proximity to the bone defect (e.g., positioning the bone screw so that it contacts the intraosseous space of a bone, and/or, in the treatment of a fracture, spans the fracture line); b) introducing a flowable medium (e.g., a bone void filler material, a cement, or a pharmaceutical agent, such as by use of a manifold of the invention (see below)) into the interior channel of the bone screw; c) allowing the flowable medium to be extruded through the delivery channels (e.g., the flowable medium is extruded through substantially all or a plurality of the delivery channels, e.g., in substantially equal volumes), and d) allowing the flowable medium to harden, thereby fixing the bone screw in place. The bone screw of the invention may be used, e.g., for maxillomandibular or craniofacial fixation, temporary fixation for repairing a bone defect in a staged reconstruction, glenoid or humeral fixation, patellar fixation, or spine fixation.

For vertebral fixation, the bone screw may be placed within a pedicle, used to anchor an interbody device, used to anchor spinal fusion plates and spacer replacement, used in an osteoporotic vertebra, or positioned in proximity to the spinous processes of adjacent vertebrae.

The method of treatment using a bone screw of the invention may also include the insertion of a rod, pin, nail, or bone plate in proximity to the bone defect. One or more of these devices may be used in conjunction with the bone screw or separate from the bone screw.

When the method is performed to provide compressive fixation, the method may include, prior to step a), i) positioning a washer (e.g., a washer of the invention) over the proximal end of the bone screw (near the screw head), ii) inserting the distal end of the bone screw into the bone so that it passes through the fracture line, and iii) tightening the bone screw such that the distal threads of the bone screw provide compressive force that pulls the bone screw head (and the washer) against the surface of the patient's bone (e.g., contact of the circumferential lip of the washer (see, e.g., FIG. 8) to the surface of the patient's bone holds the proximal end of the bone screw in place).

When the method is performed using a manifold of the invention, the method may, prior to step b) above, further include i) fluidically coupling the screw head to the sheath portion of a delivery manifold of the invention, ii) fluidically coupling an injection device, such as a syringe, that includes a flowable medium (e.g., a bone cement, such as a self-setting, injectable calcium phosphate-based bone cement (e.g., BETA-BSM™ and CARRIGEN™)) to the sheath adapter portion of a delivery manifold of the invention, iii) inserting the sheath adapter into the sheath, iv) threading the third attachment portion of the sheath adapter to the second attachment portion of the sheath to form a fluid tight seal, and v) injecting the flowable medium into the interior channel of the bone screw using, e.g., manual pressure, which results in extrusion of the bone cement through delivery channels in the bone screw. The flowable medium flows substantially evenly around the bone screw exterior (along the exterior grooves (e.g., helical grooves)) and into the bone defect. The flowable medium subsequently hardens to provide substantially fixation of the bone screw and the patient's bone. The manifold is removed from the bone screw and the surgical site is closed.

The method may also, optionally, include, prior to step d) above, i) inserting a rotational driver into the screw head (e.g., through the sheath of the manifold after removal of the sheath adapter); ii) engaging the screw head with the rotational driver; and iii) tightening the bone screw into final position by rotating the rotational driver.

Kits

The invention also features a kit that includes one or more of i) a bone screw of the invention, iii) a manifold of the invention (e.g., the sheath and sheath adapter portions), and iii) a washer of the invention. The kit may, optionally, include one or more of an injection device (e.g., a syringe), a powder of a flowable medium (e.g., a self-hardening bone cement powder), and a physiologically acceptable fluid for hydrating the bone cement powder. The flowable medium may be provided in the form of a powder that may be hydrated with a pharmaceutically acceptable fluid (e.g., water, serum, or saline) prior to use, or in a ready to use form (e.g., a paste, putty, or slurry). The kit may further include instructions for use of the bone screw, manifold, and/or washer to treat a bone defect (e.g., subarticular fracture, a defect of the spine or vertebra, or a defect of the radius, ulna, fibula, clavicle, humerus, pelvis, femur, patella, tibia, talus, calcaneus, navicular, cuneiforms, metatarsals, metacarpals, phalanges, scapula, ankle, teeth, or mandible).

Operation

The operation of bone screw 100 in combination with sheath 200 and sheath adapter 300 portions of the bone screw manifold allows for several advantages. Bone screw 100 provides an even distribution of bone cement throughout the delivery channels and along screw body 102 upon injection of bone cement into bone screw 100. Use of the manifold of the invention with the bone screw of the invention allows for the reliable injection of a flowable medium into bone screw 100 with manual pressure. Once the flowable medium has hardened, a self-cutting edge that is present along the edge of one or more of the exterior groove(s) (i.e., the edge is not radiused), as well as a self-cutting edge in the threads of the first attachment portion 110, facilitates removal of bone screw 100 without substantial damage to the newly hardened material or the bone screw itself.

In one exemplary method, bone screw 100 is provided in proximity of the bone defect. Self-tapping tip configuration 132 facilitates installation of bone screw 100 into the bone defect, e.g., with a pilot hole or with a hole smaller than the diameter of bone screw 100. A rotational driver can be used to move a bone screw into final or near-final position. The rotational driver can be disconnected and sheath 200 then attached to screw head 108 by turning first handling portion 210 manually. Sheath adapter 300 is then inserted into sheath 200 and manually tightened into place by engaging second attachment portion 210 of sheath 200 to third attachment portion 326 of sheath adapter 300. An injection device, such as a syringe, filled with a flowable medium may be attached to fourth attachment portion 318 and the injection device manually tightened into place (attachment of the injection device may also precede insertion of sheath adapter 300 into sheath 200). The stable assembly (see FIGS. 12-15 for examples of assembly of bone screw 100, sheath 200, and sheath adapter 300) of bone screw 100, sheath 200, sheath adapter 300, and an injection device facilitates injection of a flowable medium, such as a bone cement, into, through, and to the exterior of, the bone screw body 102, thereby repairing the bone defect or fracture. After injection, the injection device, sheath adapter and sheath may be disassembled to provide access to screw head 108 for further adjustment. Alternatively, the injection device and sheath adapter 300 may be disassembled and a rotational driver inserted into screw head 108 through sheath 200. If necessary, after the flowable medium has been allowed to harden, bone screw 100 can be removed, aided by a self-cutting edge of helical groove(s) 114, 115 and the self-cutting edge of the threads of first attachment portion 110.

In another exemplary method, bone screw 100 is provided in proximity to a bone defect. Prior to insertion into the bone, bone screw 100 is inserted through internal diameter 404 of bone screw washer 400. Bone screw washer 400 engages screw head 108. Self-tapping tip configuration 132 facilitates entrance of bone screw 100 into the bone defect. Threads of third threaded portion 118 and washer lip 412 provide oppositional forces as the screw is tightened in place, thereby compressing the bone defect or fracture together. A rotational driver can be used to move the bone screw into final or near-final position and achieve optimal compression of the bone defect. The injection of a flowable medium and disassembly of the bone screw 100, sheath 200, sheath adapter 300, and injection device can occur as described above.

The bone screws of the present invention provide numerous advantages over other bone screws known in the art. For example, in some embodiments of the bone screws of the present invention, the diameter of the interior channel is smaller than in cannulated bone screws in the art, resulting in improved strength and the option of reduced overall screw size. In addition, by having a smaller interior channel diameter, bone screws of the present invention are optimized for use with state-of-the-art bone cements, e.g., fourth-generation self-hardening calcium phosphate-based bone cements, which have reduced viscosity, and thus require application of less pressure than older bone cements. In additional embodiments, the threaded screw head allows for airtight attachment of a removable delivery manifold, e.g., a plastic manifold, which, in turn, facilitates loading of flowable medium by allowing a surgeon or other user to apply manual pressure rather than hydraulic pressure. This reduces the likelihood of unwanted introduction of air embolisms into the bone cavity or other surgical site. In addition, unlike prior art screws that require connection of a delivery manifold inside the rotational driver, producing very small orifices and correspondingly high operating pressure, bone screws of the present invention have no restriction in the flow path of the flowable medium, reducing the necessary operating pressure.

It is also significantly easier to remove, or to adjust the position of, a bone screw of the present invention that has been placed in a surgical site, in comparison to bone screws of the prior art. Because the rotational driver is inserted inside the screw head, it is not necessary to grasp the external surface of the screw head in order to remove an implanted screw prior to hardening of the cement.

Upon hardening of the cement around a bone screw of the present invention, the bone screw is more stable and secure than a conventional screw because of the even distribution of cement that covers a large percentage of the surface area of the screw body and contacted bone. This increased stability reduces the likelihood of "backout" of a screw from the surgical site, which may occur with a conventional screw.

In additional embodiments, the presence of exterior grooves facilitates equalized distribution of flowable medium along the exterior surface of the screw. For example, if one exterior opening is blocked, flowable medium from an adjacent exterior opening may flow along an exterior groove to "back-fill" or compensate for the blocked opening. The presence of exterior grooves, in particular, straight exterior grooves, can also increase the strength characteristics of the screw body.

In additional embodiments, use of an adjustable interior plug allows for selective delivery of flowable medium to desired delivery channels while blocking off other delivery channels. Such a plug may be designed to be pushed in or screwed in and may be either permanent or removable. In addition, in some embodiments, the tip or distal end of the screw body, i.e., the end of the screw body distal to the screw head, may be manufactured to be open or closed; in open embodiments, a removable tip plug may be added as needed according to the surgical indication. The inclusion of such adjustable plugs significantly increases the flexibility of use of bone screws of the present invention.

EXAMPLES

The following examples are to illustrate the invention. They are not meant to limit the invention in any way.

Example 1: Use of a Bone Screw of the Invention to Repair a Fracture or Other Bone Defect A bone screw of the invention (e.g., a bone screw of FIGS. 1-5) can be used to provide fracture support, e.g., for a subarticular fracture, in conjunction with conventional fixation. The site to be supported can be accessed using either a percutaneous or open technique. The extraction technique preferably ensures maximal bone conservation.

Example 2: Use of a Bone Screw of the Invention for Compression Fixation

A bone screw of the invention can be used for compression fixation in combination with a washer of the invention to repair a hip fracture. The fractured bone is aligned and held in the proper position by traction.

A bone screw of the invention is inserted into a washer of the invention. The surgical site is prepared (e.g., by reaming or drilling) to accept the bone screw and body of the washer. The bone screw tip is inserted into the bone such that the threaded portion at the distal end of the body of the bone screw passes beyond the fracture line and into the femoral head. Tightening of the bone screw forces the circumferential lip of the washer against the exterior surface of the bone, which compresses the bone above and below the fracture line, thereby providing compression fixation. A bone cement is injected into the head of the bone screw (e.g., using a manifold of the invention), and hardening of the bone cement fixes the bone screw in place.

Example 3: Use of a Bone Screw of the Invention to Repair a Fracture or Other Bone Defect with Manual Pressure A bone model system was used to experimentally determine the forces required to inject a flowable material into a bone screw of the inventive method.

The clinical objective of bone screws of the invention is to provide secure fixation across a fracture and to enable delivery of a Bone Void Filler (BVF) to the surrounding defect area. It is standard of care to reduce fractures with 4 mm diameter fixation screws. These screws are often used together with BVF material injected around the screw into the fracture site to fill voids.

Figure 9:
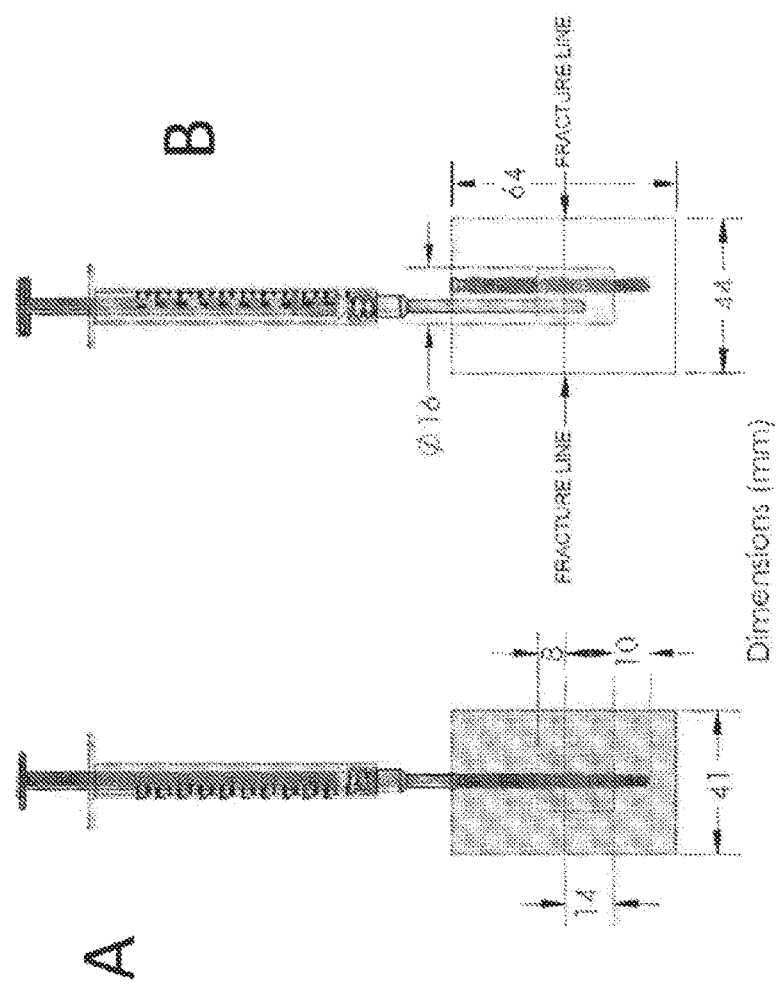
FIGS. 9A and 9B are schematics showing testing of a bone screw of the invention using a bone void model (with dimensions shown).

We created bone void models (BVM) to simulate a 4.5 milliliter (mL) defect. We used a closed cell 12.5 PCF bone foam to represent typical metaphyseal cancellous bone. Foam blocks were split in half and a hole drilled into each side to form a 4.5 mL hollow cavity when assembled together (FIG. 9).

The distal end of the bone screw is typically embedded into the distal fragment by approximately 10 mm. Screws are placed through the center of the void such that the distal end of the screw was located approximately 10 mm past the void. Four smaller (1.5 mL) bone void models were constructed similarly to the 4.5 mL models. BVF was also tested in these models to verify the ability to fill smaller voids through the screw even if fewer holes are exposed to the void.

Static extraction torque testing was performed to demonstrate the bone screw can be removed without damaging the screw or the surrounding BVF. Testing was also performed using CARRIGEN™ to evaluate static extraction torque with this BVF.

Delivery of BVF Through 11 Gauge Cannula

Figure 10:
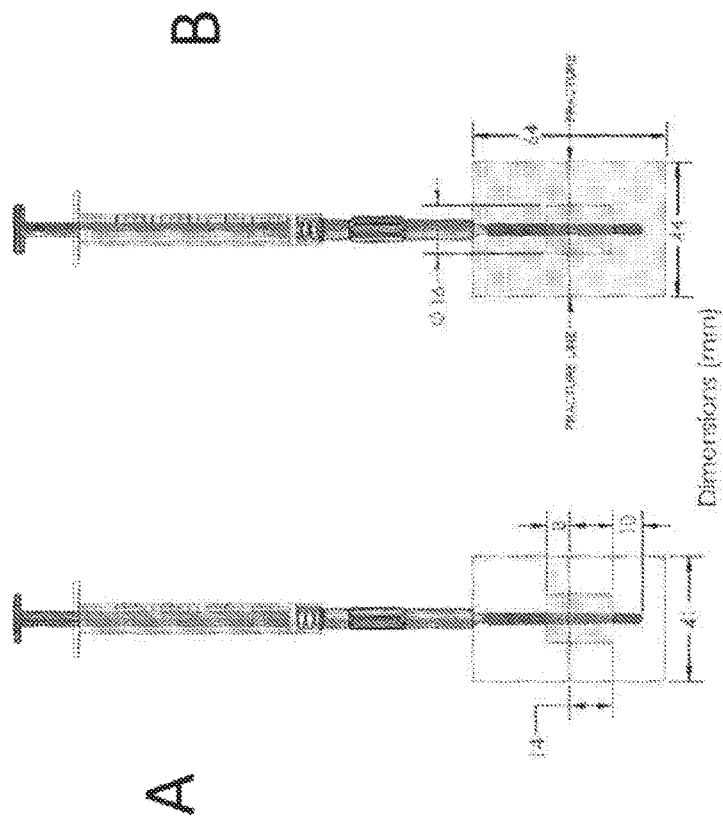
FIGS. 10A and 10B are schematics showing testing of a bone screw of the invention attached to a bone screw manifold of the invention in the bone void model (with dimensions shown).

A test set up was constructed as shown in FIGS. 9 and 10 consisting of a 50 mm length by 4 mm diameter fixation screw, an injection needle, foam test block construct, insertion syringe, and BVF. This test set up simulated the current standard of care method for delivery of BVF during a bone void filling procedure. Test blocks were constructed from foam mimicking cancellous bone (PCF 12.5 polyurethane). A 44 mm×64 mm×41 mm block was split in half and a 16 mm diameter hole drilled into each side to total depth of 22 mm to form a 4.5 mL hollow cavity when assembled together. The two halves of the model were clamped together using 2" drywall screws, external to the void. The fixation screw was inserted through the center of the defect to a depth of approximately 10 mm fixation in the distal block.

The injection needle was then inserted into the specimen adjacent to the screw into the void. The BVF was prepared according to the manufacturer's Instructions for Use. The BVF was loaded into the syringes. To simulate worst case handling of the materials, each was left at room temperature in a mixed condition for the maximum allowed per the manufacturer's Instructions for Use (BETA-BSM™—2 minutes; CARRIGEN™—15 minutes). Each was then attached to the luer lock of the needle and injected under finger pressure into the needle/test block assembly. Injection pressure was measured according to the protocol according to Example 4. The stylet was inserted into the needle to expel residual BVF within the needle. The test samples were then placed in a 37° C. incubator for two hours to allow the BVF to harden. Mass of the specimen was measured before and after BVF injection to determine amount of fill of the BVF into the specimen. The specimens were imaged using C-arm fluoroscopy.

The static torque extraction tests were performed by hand using calibrated torque wrench. The peak torque required to loosen each screw from the foam test blocks was recorded. The specimens were then sectioned to assess the fill of the void and any damage to the BVF after screw removal.

Delivery of BVF Through the Bone Screw

A test set up was constructed as shown in FIGS. 9 and 10 consisting of a 50 mm length N-force by 4 mm diameter fixation screw, screw sheath, foam test block construct, insertion syringe, and BVF. This test set up simulated delivery of BVF during a bone void filling procedure through the bone screw. Test blocks were constructed from foam mimicking cancellous bone (PCF 12.5 polyurethane). A 44 mm×64 mm×41 mm block was split in half and a 16 mm hole drilled into each side for a total depth of 22 mm to form a 4.5 mL hollow cavity when assembled together. The halves of the model were clamped together using 2" drywall screws, external to the void. The fixation screw was inserted through the center of the defect to a depth of approximately 10 mm fixation in the distal block. The BVF was prepared according to the manufacturer's Instructions for Use. The BVF was loaded into the syringes. To simulate worst case handling of the materials, each was left at room temperature in a mixed condition for the maximum allowed per the manufacturer's Instructions for Use (BETA-BSM™-2 minutes; CARRIGEN™-15 minutes). Each was then attached to the luer lock of the sheath and injected under finger pressure into the screw/test block assembly. Delivery pressure was measured per the protocol described in Example 4. The hex driver was inserted through the sheath into the screw to expel residual BVF within the sheath. The test samples were then placed in a 37° C. incubator for two hours to allow the BVF to harden.

Mass of the specimen was measured before and after BVF injection to determine amount of fill of the BVF into the specimen. The specimens were imaged using C-arm fluoroscopy. The static torque extraction tests were performed by hand using calibrated torque wrench. The peak torque required to loosen each screw from the foam test blocks was recorded. The specimens were then sectioned to assess the fill of the void and any damage to the BVF after screw removal. The results are shown in Table 1 below.

Delivery Force Measurement Procedure

The force required to deliver BVF throughout the length of a bone screw of the invention was compared to a simple cannula. Twelve kits containing the respective bone void fillers BETA-BSM™ and CARRIGEN™ were used to conduct the experiments. The simple cannula used was a 63.5 mm×11 Gauge cannulae (Hamilton Corp, Part #: 7750-02).

The bone screws had were 4 mm (internal diameter)×50 mm in length. The bone void models (BVM) were used as described in Example 3. Four smaller 1.5 mL simulated bone void models were constructed similarly to the 4.5 mL models but the 16 mm holes were drilled to a depth of 3.75 mm.

The bone void fillers, BETA-BSM™ and CARRIGEN™, were prepared using commercial kit components per the mixing instructions from the manufacturers. BETA-BSM™ was left in the 10 mL mixing/delivery syringe which is supplied with the kit. The resulting material from each CARRIGEN™ kit was transferred into five 1 mL syringes. The filled syringes were attached to bone screws or cannulae which had been placed in the bone models as shown in FIGS. 9 and 10. Injectability testing was performed by placing the syringe with the BVM attached into a support frame. The syringe plunger was moved using the measurement end of a force measuring device. The Average and maximum injection force was measured using a uniaxial load frame. Delivered mass was measured by weighing the bone model before and after delivery. Delivered volume was calculated by dividing the delivered mass by the appropriate material density (1.8 g/mL for CARRIGEN™, 1.6 g/mL for BETA-BSM™). For each product (BETA-BSM™ and CARRIGEN™) five of the kits were delivered through a cannula and five delivered through a bone screw. Statistical analysis was performed on the resulting data using STATGRAPHICS Plus 4.1 for Windows. An additional 2 kits of each product were delivered through bone screws into the small defect models to verify the defect size did not impact the results.

No difference was seen in the performance of BETA-BSM™ and CARRIGEN™ BVF's delivered via the bone screws with respect to their ability deliver with digital pressure and to fill a bone void relative to delivery through an 11 gauge cannula. Screws of this invention could be removed from defects filled with hardened BETA-BSM™ and CARRIGEN™ BVF without damaging the screws or BVF.

TABLE 1

Summary of Results

| Parameter | BVF: BETA-BSM ™ | | BVF: CARRIGEN ™ | |
| --- | --- | --- | --- | --- |
| | Inventive Bone Screw | Cannula | Inventive Bone Screw | Cannula |
| Average Delivery Force (kgf) | 1.25 ± 0.18 | 0.91 ± 0.19 | 1.57 ± 0.14 | 1.31 ± 0.08 |
| Maximum Delivery Force (kgf) | 2.05 ± 0.23 | 2.09 ± 0.53 | 2.17 ± 0.34 | 1.74 ± 0.10 |
| Delivered Mass (g) | 7.42 ± 0.14 | 7.58 ± 0.10 | 8.32 ± 0.29 | 8.86 ± 0.07 |
| Calculated Delivered Volume (mL) | 4.64 ± 0.09 | 4.74 ± 0.06 | 4.62 ± 0.16 | 4.92 ± 0.04 |
| Screw Removal Mean Peak Torque (Nmm) | 1,360 ± 153 | 1,300 ± 68 | 1,710 ± 204 | 1,520 ± 102 |

Results

Acceptance criteria for delivery pressure (digital pressure) was set at 10 kgf based on previous design criteria for BETA-BSM™ and product release. Delivery force values for all samples were well below this limit as seen in the Table 1. All samples exhibited 100% injection and were delivered into the void by digital pressure (<10 Kgf) through both the 11 gauge cannula and the bone screws.

Figure 11:
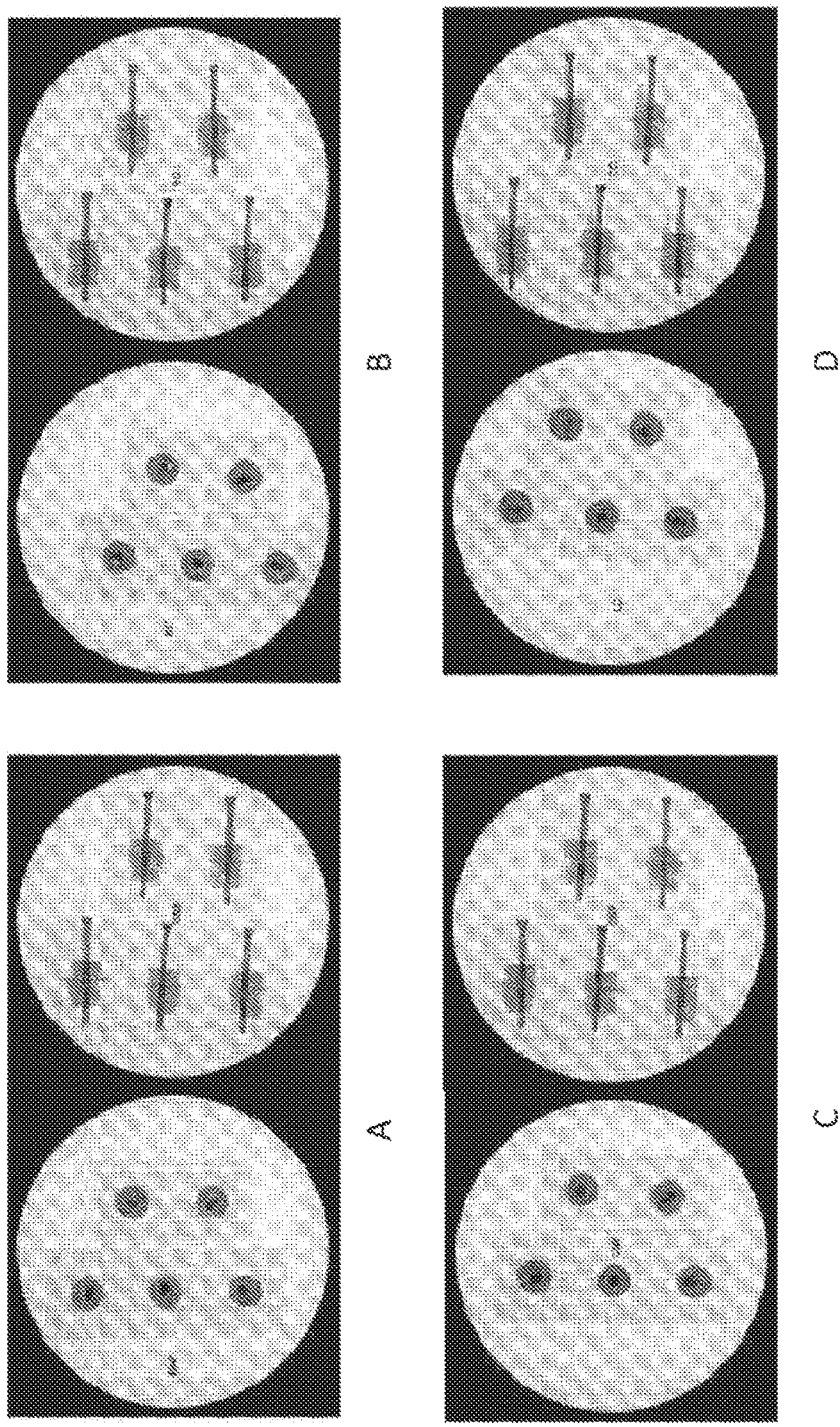
FIGS. 11A-11D are fluoroscopy images showing the results of the testing of the bone screw of the invention using a bone void model.
Figure 12:
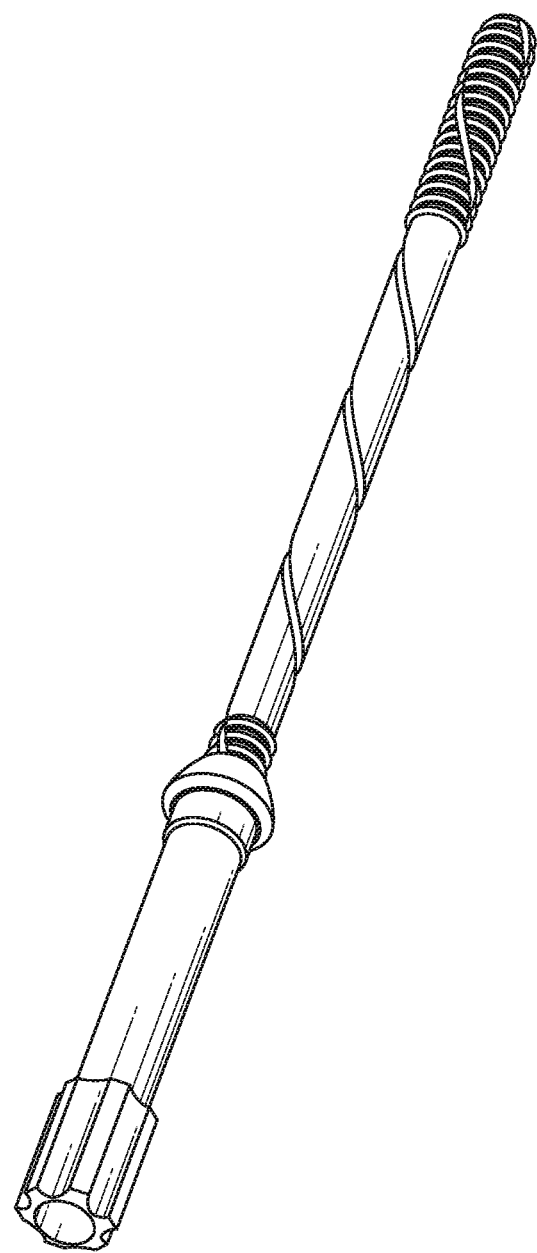
FIG. 12 is a photograph showing attachment of the sheath portion of a manifold of the invention to a bone screw of the invention.
Figure 13:
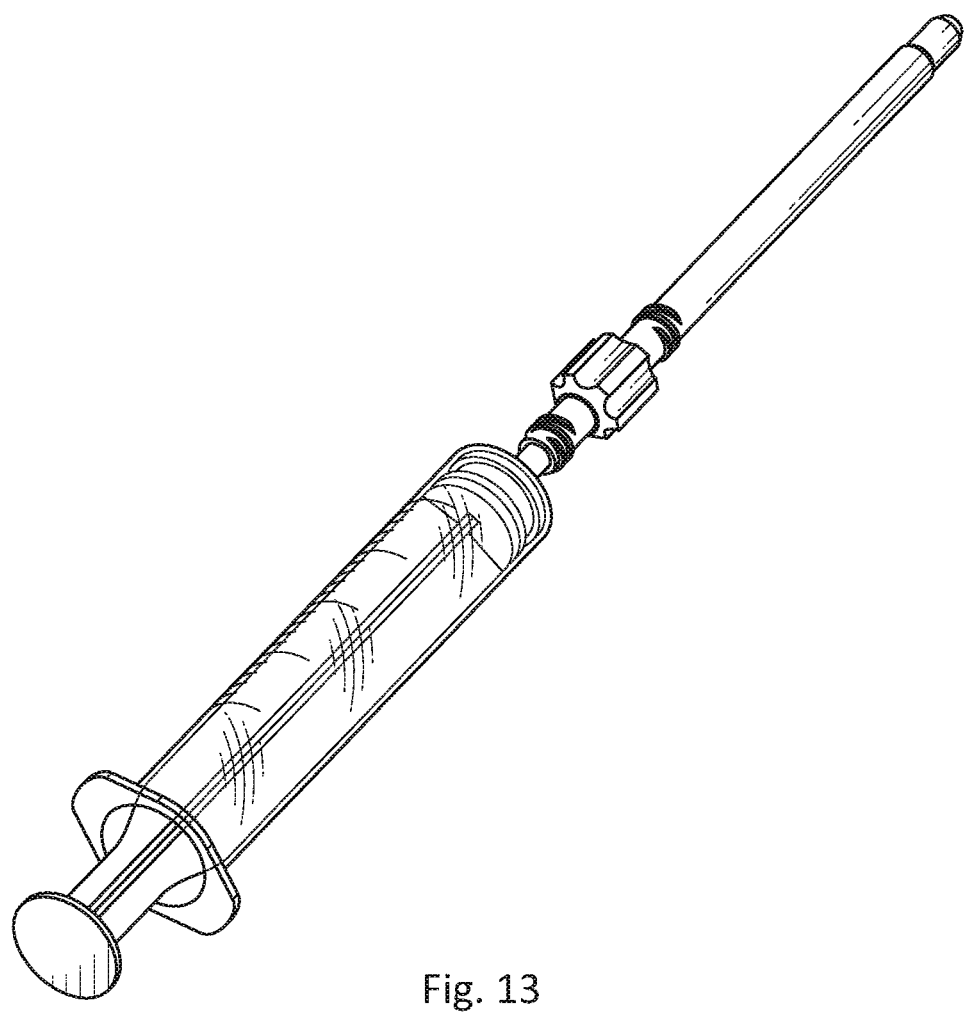
FIG. 13 is a photograph showing attachment of an injection device (a syringe) to the sheath adapter portion of a manifold of the invention.
Figure 14:
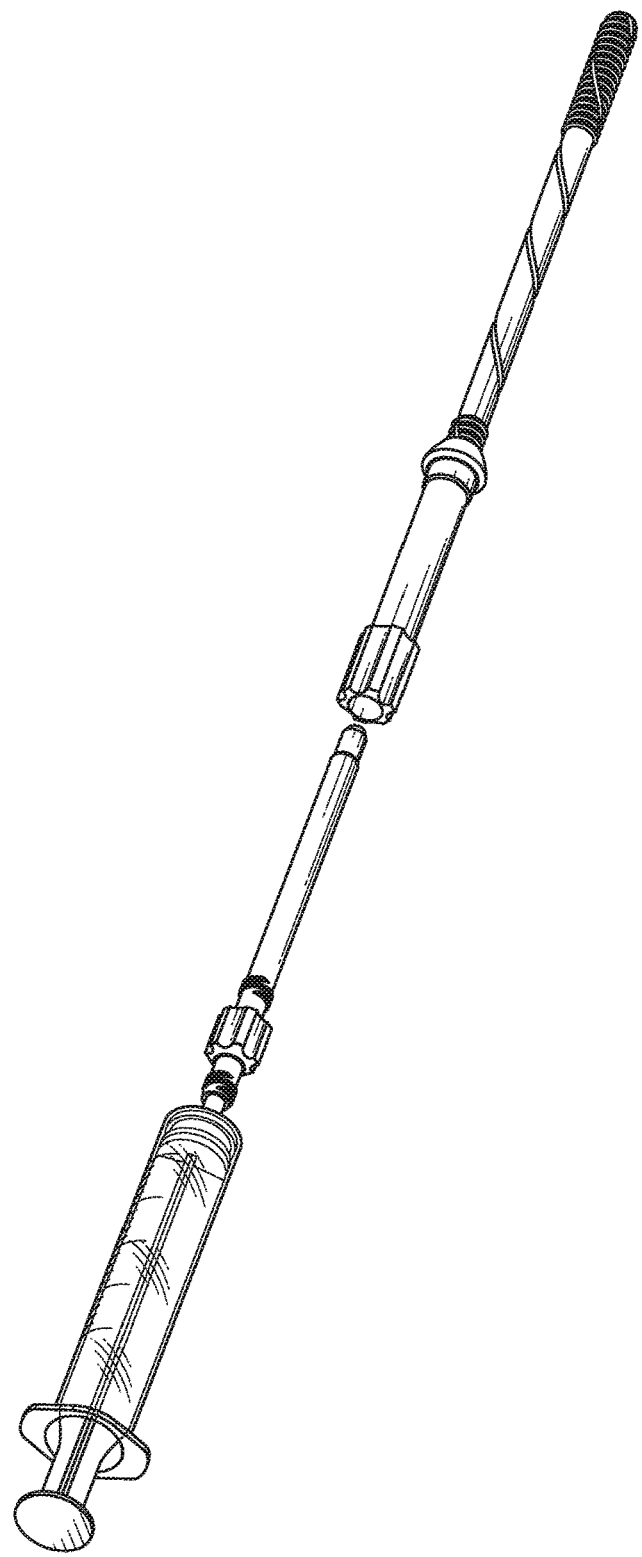
FIG. 14 is a photograph showing insertion of the sheath adapter of FIG. 13 into the sheath of FIG. 12.
Figure 15:
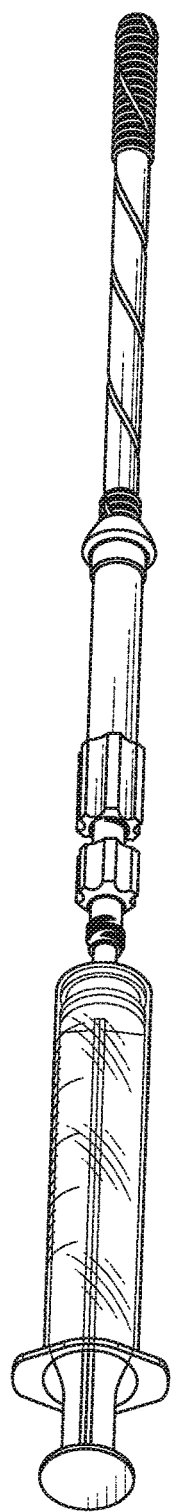
FIG. 15 is a photograph showing complete assembly of the manifold (sheath+sheath adapter) and the bone screw.

The bone fillers, BETA-BSM™ and CARRIGEN™, both filled the 4.5 mL BVM regardless of whether delivered through an 11 gauge Cannula or the bone screw. Table 1 shows that both delivery methods delivered at least 4.5 mL of BVF to the bone void model. All samples exhibited delivered volumes greater than 4.5 mL, the volume of the defect. In addition to the void fill measurement, visual inspection was made of the samples through fluoroscopy images and digital images after sectioning. The fluoroscopy images, in FIG. 11, showed that BETA-BSM™ and CARRIGEN™ achieved proper fill of the 4.5 mL defect regardless of delivery through an 11 gauge cannula or through the bone screw. Visual inspection of the sectioned samples also showed the voids were filled with BETA-BSM™ or CARRIGEN™ regardless of delivery through an 11 gauge cannula or the bone screw.

Screw removal testing (Table 1) showed that the bone screws could be removed from hardened BETA-BSM™ and hardened CARRIGEN™ at clinically acceptable torques (mean peak removal torque) regardless of delivery through an 11 gauge cannula or the bone screw. All of the removal torques were well below the mean torque to failure (screw fracture) of the screw of 2,960±27 Nmm. Visual inspection showed that screw removal did no damage to the hardened BVF. The thread forms were still visible after screw removal.

Results from sampling (n=2) small void models (1.5 mL) showed that both BVF's were able to fill a small void through the N-Force screws even with fewer fenestrations contacting the void. Also, delivery pressures and screw removal torques were well within limits described in Table 1.

Example 4: Strength of Inventive Bone Screw

Mechanical Testing Methodology

Bone screws of the invention were tested to confirm the retention of mechanical properties after being fenestrated. Five screws with the dimensions 7 mm×130 mm were tested in accordance with ASTM method ASTM F1264-03(2012). Specifically, the static 4-point bend tests were completed as outlined in ASTM F1264-03(2012). They were performed in stroke control at a rate of 6 mm per minute starting at zero load and continuing until failure. Force vs. displacement data were recorded throughout test duration. The support span was 114 mm, the span between loading points was 38 mm, the load to support span was 38 mm, and the roller diameter was 12.6 mm.

Results

The results show that the bone screws exhibit a mean bending stiffness of 172 N/mm, a mean bending yield force of 886 N, a mean bending yield moment of 16.8 Nm, a mean bending structural stiffness of 3.93 Nm2, a mean bending ultimate force of 1,173 N and a mean bending ultimate moment of 22.3 Nm. Failure mode was the screw yielding. The mechanical results show that bone screws of the invention are compatible for use in the repair of bone defects, such as in fracture fixation.

OTHER EMBODIMENTS

All publications, patents, and patent applications mentioned in the above specification are hereby incorporated by reference, including U.S. Application Publication No. 2011/0060373. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A bone screw having a length from about 60 millimeters (mm) to 200 mm and comprising: i) a cylindrical screw body comprising a shaft that defines a longitudinal axis, ii) a screw head at the proximal end of said screw body, and iii) a tip at the distal end of said screw body, said bone screw further comprising:
   a) an interior channel extending longitudinally through said screw head and through at least a portion of the shaft of said screw body, wherein said interior channel has a diameter of about 3 to 5 mm;
   b) a first threaded portion on the exterior of said screw head extending from about the proximal end of said screw head along at least a portion of the screw head;
   c) a second threaded portion on the exterior of said screw body adjacent to the screw head that extends in a direction along the screw body away from said screw head and having one or more delivery channels;
   d) a third threaded portion on the exterior of said screw body adjacent to the tip that extends along a distal portion of the screw body and having one or more delivery channels;
   e) a non-threaded portion between the second and third threaded portions on the exterior of said screw body and having one or more delivery channels; and
   f) at least first and second helical grooves extending along the exterior of said screw body, wherein:
      i) said first helical groove is substantially anti-parallel to said second helical groove and said helical grooves extend continuously through said second threaded portion, said non-threaded portion, and at least a portion of said third threaded portion,
      ii) said delivery channels are coincident with said helical grooves,
      iii) each of said delivery channels within the helical grooves of said non-threaded portion is separated by a distance of about 18 to 24 mm along said helical groove, and
      iv) each of said delivery channels of said third threaded portion is separated by a distance of about 5 to 7 mm along said helical groove.

2. The bone screw of claim 1, wherein said bone screw comprises one or more, or all, of the following characteristics:
   a) each of said delivery channels has a diameter of about 0.5 to 2 mm;
   b) said screw head has a length of about 4 to 7 mm and said first threaded portion has a length of about 2 to 4 mm and an exterior diameter of about 6 to 10 mm;
   c) said second threaded portion comprises about 2 to 4 thread revolutions, 1 to 4 delivery channels and a length of about 5 to 8 mm;
   d) said third threaded portion comprises about 10 to 20 thread revolutions, 8 to 12 delivery channels and a length of about 25 to 40 mm;
   e) said non-threaded portion has a length of about 16 to 86 mm;
   f) the ratio of said delivery channels in said third threaded portion to said non-threaded portion is at least 1.25:1;
   g) said bone screw has a length of about 60 to 130 mm;
   h) said first threaded portion comprises about 1 to 5 thread revolutions;
   i) said delivery channels are not within about 5 mm of the proximal end and distal end of said bone screw; and/or
   j) each of said delivery channels within the helical grooves of said non-threaded portion is separated by a distance of about 18 to 24 mm along said helical groove.

3. The bone screw of claim 1, wherein said bone screw comprises one or more, or all, of the following characteristics:
   a) said interior channel has a diameter of about 3.9 mm;
   b) said screw head has a length of about 5.3 mm and said first threaded portion has a length of about 3.2 mm and an exterior diameter of 8.3 mm;
   c) said second threaded portion comprises about 3 thread revolutions, about 2 delivery channels and a length of about 6.5 mm;
   d) said third threaded portion comprises about 16 thread revolutions, about 10 delivery channels and a length of about 32 mm and each of said delivery channels of said third threaded portion is separated by a distance of about 6 mm along said helical grooves;
   e) said non-threaded portion has a length of about 16 mm to 86 mm and comprises at least one to about 24 delivery channels and each of said delivery channels of said non-threaded portion is separated by a distance of about 21 mm along said helical grooves; and/or
   f) each of said delivery channels has a diameter of about 1.2 mm.

4. The bone screw of claim 1, wherein:
   a) said delivery channels are distributed along said helical grooves to provide substantially equal distribution of a flowable medium extruded through each of said delivery channels following introduction of said flowable medium through said screw head into said interior channel;
   b) said bone screw is, or comprises, stainless steel alloy, titanium alloy, commercially pure titanium, cobalt chrome, or polyetheretherketone, or combinations thereof;
   c) each of said delivery channels is tapered along at least a portion of its radial axis or is substantially cylindrical;
   d) at least one edge of said helical grooves comprises a self-cutting edge; and/or
   e) said bone screw has a mean bending stiffness of at least 136 N/mm in a 4-point bend test.

5. The bone screw of claim 4, wherein the flowable medium comprises a bone void filler, a cement, or a pharmaceutical agent.

6. The bone screw of claim 5, wherein the cement is a self-hardening calcium phosphate composition.

7. A method of treating a patient having a bone defect, said method comprising the steps of:
   a) positioning the bone screw of claim 1 in proximity to said bone defect;
   b) attaching a bone screw manifold comprising a sheath and a sheath adapter for delivering a fluid to the bone screw, comprising:
      i) attaching the sheath to the screw head of the bone screw, wherein the sheath comprises a cylindrical sheath body that defines a longitudinal axis, a first attachment portion at the distal end of the sheath body, a second attachment portion at the proximal end of the sheath body, and an internal channel having a diameter of at least about 5 mm that extends continuously through the sheath body and through the first and second attachment portions to provide fluid communication through the manifold, wherein:

the sheath body has a length of about 60 to 90 mm;
the first attachment portion comprises a threaded region within the internal channel; and
the second attachment portion comprises a threaded region within the internal channel, and comprises a first handling portion on the exterior of at least a portion of the second attachment portion; and ii) attaching the sheath adapter to the sheath, wherein the sheath adapter comprises a cylindrical sheath adapter body that defines a longitudinal axis, a third attachment portion at the proximal end of the sheath adapter body, a second handling portion adjacent to the third attachment portion, a fourth attachment portion adjacent to the second handling portion, a tapered portion at the distal end of the sheath adapter body, and an internal channel having a diameter of at least about 2 mm that extends continuously through the sheath adapter body, the third attachment portion, the second handling portion, the fourth attachment portion, and the tapered portion to provide fluid communication through the sheath adapter, wherein:
the sheath adapter body has a length of about 50 to 80 mm and an external diameter that is less than the diameter of the internal channel of the sheath;
the third attachment portion comprises a threaded region on an exterior portion thereof;
the second handling portion comprises raised ridges on an exterior portion thereof; and
the fourth attachment portion comprises a threaded region on an exterior portion thereof; and
wherein the sheath adapter body is sized and shaped for insertion into the internal channel of the sheath, the threaded region of said third attachment portion of the sheath adapter is sized and shaped to be threadingly engaged with the threaded region of the second attachment portion of the sheath, thereby reversibly joining the sheath and the sheath adapter when engaged, and, when the sheath and the sheath adapter are joined, the tapered portion of the sheath adapter extends into the first attachment portion of the sheath;

c) attaching a manual pressure injection device that includes a flowable medium to said fourth attachment portion of said sheath adapter; and d) introducing the flowable medium into said interior channel of said bone screw by applying manual pressure to the injection device, whereby said flowable material is extruded through said delivery channels; wherein hardening of said flowable medium secures said bone screw, thereby treating said bone defect in said patient.

8. The method of claim 7, wherein the flowable medium is a bone void filler, a cement, or a pharmaceutical agent.

9. The method of claim 8, wherein the cement is a self-hardening calcium phosphate composition.

10. The method of claim 7, wherein the bone detect comprises a subarticular fracture or a defect of the radius, ulna, fibula, clavicle, humerus, pelvis, femur, patella, tibia, talus, Calcaneus, navicular, cuneiforms, metatarsals, metacarpals, phalanges, scapula, ankle or vertebra; or is a compression fracture.

11. The method of claim 7, further comprising, prior to step a), joining a washer to said screw head, wherein said washer is sized is sized and shaped to accept said screw head of said bone screw and to engage a bone surface.

12. The method of claim 11, wherein said washer comprises:
a) a cylindrical body comprising a shaft that defines a longitudinal axis, wherein said body has a length of about 5 to 8 mm and a diameter of 7 to 10.5 mm;
b) a bone engaging portion at the proximal end of the body comprising a circumferential lip with a thickness of 1 to 2 mm and a radial diameter of 10 to 15 mm; and
c) a screw head engaging portion at the distal end of the body having a diameter of 6 to 9 mm, wherein the diameter of the screw head engaging portion is less than the diameter of the body.

13. A system comprising the bone screw of claim 1 wherein said system comprises one or more of a bone screw manifold, a bone screw washer, an injection device, a flowable medium, a self-hardening bone cement powder, and instructions for using said system.

14. A bone screw manifold comprising a sheath and a sheath adapter for delivering a flowable medium to a cannulated and fenestrated bone screw, wherein:
a) said sheath comprises a cylindrical sheath body that defines a longitudinal axis, a first attachment portion at the distal end of said sheath body, a second attachment portion at the proximal end of said sheath body, and an internal channel having a diameter of at least about 5 mm that extends continuously through said sheath body and through said first and second attachment portions to provide fluid communication through said manifold, wherein:
i) said sheath body has a length of about 60 to 90 mm;
ii) said first attachment portion comprises a threaded region within said internal channel; and
iii) said second attachment portion comprises a threaded region within said internal channel, and comprises a first handling portion on the exterior of at least a portion of said second attachment portion; and
b) said sheath adapter comprises a cylindrical sheath adapter body that defines a longitudinal axis, a third attachment portion at the proximal end of said sheath adapter body, a second handling portion adjacent to said third attachment portion, a fourth attachment portion adjacent to said second handling portion, a tapered portion at the distal end of said sheath adapter body, and an internal channel having a diameter of at least about 2 mm that extends continuously through said sheath adapter body, said third attachment portion, said second handling portion, said fourth attachment portion, and said tapered portion to provide fluid communication through said sheath adapter, wherein:
i) said sheath adapter body has a length of about 50 to 80 mm and an external diameter that is less than the diameter of the internal channel of said sheath;
ii) said third attachment portion comprises a threaded region on an exterior portion thereof;
iii) said second handling portion comprises raised ridges on an exterior portion thereof; and
iv) said fourth attachment portion comprises a threaded region on an exterior portion thereof; and
wherein the sheath adapter body is sized and shaped for insertion into the internal channel of said sheath, the threaded region of said third attachment portion of said sheath adapter is sized and shaped to be threadingly engaged with the threaded region of said second attachment portion of said sheath, thereby reversibly joining said sheath and said sheath adapter when engaged, and, when said sheath and said sheath adapter are joined, said tapered portion of said sheath adapter extends into said first attachment portion of said sheath, and wherein said manifold is capable of delivering said flowable medium to the distal tip of the cannulated and fenestrated bone screw having a length of at least about 130 mm using manual pressure.

15. The bone screw manifold of claim 14, wherein said bone screw manifold comprises one or more, or all, of the following characteristics:
   a) said sheath body has an external diameter of at least 8 mm;
   b) said first attachment portion has a length of about 5 to 8 mm, said threaded region of said first attachment portion has a length of about 2 to 4 mm and at least 3 thread revolutions, and said internal channel of said first attachment portion has an internal diameter of about 6 to 9 mm;
   c) said second attachment portion has a length of about 16 to 24 mm, and wherein said threaded region of said second attachment portion has a length of about 4 to 7 mm and at least 2 thread revolutions, and said internal channel of said second attachment portion has an internal diameter of about 5 to 8 mm;
   d) said first handling portion comprising at least five raised ridges that extend in a direction substantially parallel to the longitudinal axis of said sheath body;
   e) said third attachment portion has a length of about 6 to 10 mm and said threaded region of said third attachment portion has a length of about 4 to 7 mm and at least 2 thread revolutions;
   f) said second handling portion has a length of about 10 to 15 mm and comprises at least four raised ridges on an exterior portion thereof that extend in a direction substantially parallel to the longitudinal axis of said sheath adapter body;
   g) said fourth attachment portion has a length of about 6 to 9 mm and said threaded region of said fourth attachment portion has a length of about 3 to 5 mm and at least 2 thread revolutions;
   h) said tapered portion has a length of about 5 to 7 mm and an exterior diameter of about 2.5 to 7 mm, and said tapered portion has a chamfer at the distal end;
   i) said first attachment portion of said sheath is sized and shaped to be threadingly engaged with a head of the bone screw;
   j) said second attachment portion of said sheath is sized and shaped to be threadingly engaged with a device for injecting a flowable medium, wherein said flowable medium comprises a bone void filler, a cement, or a pharmaceutical agent;
   k) said bone screw manifold is, or comprises, a polymeric material;
   l) said sheath body has a length of about 76.2 mm and said internal channel of said sheath has a diameter of 5.8 mm; and/or
   m) said sheath adapter body has a length of about 67.1 mm and an external diameter of about 5.3 mm and said internal channel of said sheath adapter has a diameter of 2.5 mm.

16. A system comprising the bone screw manifold of claim 14, wherein the system comprises a bone screw and/or one or more of a bone screw washer, an injection device, a self-hardening bone cement powder, and instructions for using said system.

* * * * *